United States Patent
Dai

(10) Patent No.: US 7,189,551 B2
(45) Date of Patent: Mar. 13, 2007

(54) HUMAN RPS6KA6-RELATED GENE VARIANT ASSOCIATED WITH LUNG CANCERS

(75) Inventor: Ken-Shwo Dai, Hsinchu (TW)

(73) Assignee: Bioptik Technology, Inc., Taipei (TW)

( * ) Notice: Subject to any disclaimer, the term of this patent is extended or adjusted under 35 U.S.C. 154(b) by 395 days.

(21) Appl. No.: 10/809,075

(22) Filed: Mar. 25, 2004

(65) Prior Publication Data

US 2005/0208507 A1 Sep. 22, 2005

Related U.S. Application Data

(63) Continuation-in-part of application No. 10/102,554, filed on Mar. 20, 2002, now abandoned.

(51) Int. Cl.
| | |
|---|---|
| C12N 9/12 | (2006.01) |
| C12N 1/20 | (2006.01) |
| C12N 15/00 | (2006.01) |
| C12N 9/00 | (2006.01) |
| C07H 21/04 | (2006.01) |

(52) U.S. Cl. .................. 435/194; 435/183; 435/252.3; 435/252.32; 435/320.1; 536/23.2

(58) Field of Classification Search ................ 435/183, 435/194, 252.3, 252.32, 320.1; 536/23.2
See application file for complete search history.

(56) References Cited

U.S. PATENT DOCUMENTS

2002/0192645 A1  12/2002  Tseng et al.
2003/0180727 A1   9/2003  Dai
2004/0009481 A1   1/2004  Schlegel et al.

FOREIGN PATENT DOCUMENTS

WO    00/73469    12/2000

OTHER PUBLICATIONS

Sethi, T. "Science, Medicine and the Future: Lung Cancer." *BMJ*, 314 (7081) 652 (1997).
Yntema, H.G., et al. "A Novel Ribosomal S6-Kinase (RSK4; RPS6KA6) is Commonly Deleted in Patients . . . Retardation." *Genomics*, vol. 62, (1999) pp. 332-343.
Sundareshan, T.S., et al. "Cytogenetics of Non-Small Cell Lung Cancer: Simple Technique for Obtaining High . . . Cultures." *Cancer Genet Cytogenet*, vol. 91 (1996) pp. 53-60.
Plowman, et al., Accession AX056372 Jan. 13, 2001.
Wang, et al. Accession AR029882 Sep. 29, 1999.
Chin, A. "On the Preparation and Utilization of Isolated and Purified Oligonucleotides." [electronic resource] Allegedly deposited in UNC library on Mar. 14, 2002, date of publication, if any, is in question.
Ynterna et al. "A Novel Ribosomal S6-Kinase (RSK4; RPS6KA6) is Commonly Deleted in Patients with Complex X-Linked Mental Retardation" *Genomics* (1999) vol. 62, 332-343.

*Primary Examiner*—Tekchand Saidha
*Assistant Examiner*—Christian L. Fronda
(74) *Attorney, Agent, or Firm*—Ladas and Parry LLP

(57) ABSTRACT

The invention relates to the nucleic acid and polypeptide sequences of a novel human RPS6KA6-related gene variant (RPS6KA6V).

The invention also provides a process for producing the polypeptide of the variant.

The invention further provides a use of the nucleic acid and polypeptide sequences of the gene variant in diagnosing T-cell lymphoblastic lymphoma.

5 Claims, 15 Drawing Sheets

Fig. 1a

```
GGGAAATGCTACCATTCGCTCCTCAGGACGAGCCCTGGGACCGAGAAATGGAAGTGTTCA  60
        M  L  P  F  A  P  Q  D  E  P  W  D  R  E  M  E  V  F  S  19
GCGGCGGCGGCGCGAGCAGCGGCGAGGTAAATGGTCTTAAAATGGTTGATGAGCCAATGG  120
  G  G  G  A  S  S  G  E  V  N  G  L  K  M  V  D  E  P  M  E  39
AAGAGGGAGAAGCAGATTCTTGTCATGATGAAGGAGTTGTTAAAGAAATCCCTATTACTC  180
  E  G  E  A  D  S  C  H  D  E  G  V  V  K  E  I  P  I  T  H  59
ATCATGTTAAGGAAGGCTATGAGAAAGCAGATCCTGCACAGTTTGAGTTGCTCAAGGTTC  240
  H  V  K  E  G  Y  E  K  A  D  P  A  Q  F  E  L  L  K  V  L  79
TTGGTCAGGGGTCATTTGGAAAGGTTTTTCTTGTTAGAAAGAAGACCGGTCCTGATGCTG  300
  L  G  Q  G  S  F  G  K  V  F  L  V  R  K  K  T  G  P  D  A  G  99
GGCAGCTCTATGCAATGAAGGTGTTAAAAAAAGCCTCTTTAAAAGTTCGAGACAGAGTTC  360
  Q  L  Y  A  M  K  V  L  K  K  A  S  L  K  V  R  D  R  V  119
GGACAAAGATGGAGAGGGATATACTGGTGGAAGTAAATCATCCATTTATTGTCAAATTGC  420
  T  K  M  E  R  D  I  L  V  E  V  N  H  P  F  I  V  K  L  139
ACTATGCCTTTCAGACTGAAGGGAAACTGTACTTAATACTGGATTTTCTCAGGGGAGGAG  480
  H  Y  A  F  Q  T  E  G  K  L  Y  L  I  L  D  F  L  R  G  G  D  159
ATGTTTTCACAAGATTATCCAAAGAGGTTCTGTTTACAGAGGAAGATGTGAAATTCTACC  540
  V  F  T  R  L  S  K  E  V  L  F  T  E  E  D  V  K  F  Y  L  179
TCGCAGAACTGGCCCTTGCTTTGGATCATCTGCACCAATTAGGAATTGTTTATAGAGACC  600
  A  E  L  A  L  A  L  D  H  L  H  Q  L  G  I  V  Y  R  D  L  199
TGAAGCCAGAAAACATTTTGCTTGATGAAATAGGACATATCAAATTAACAGATTTTGGAC  660
  K  P  E  N  I  L  L  D  E  I  G  H  I  K  L  T  D  F  G  L  219
TCAGCAAGGAGTCAGTAGATCAAGAAAAGAAGGCTTACTCATTTTGTGGTACAGTAGAGT  720
  S  K  E  S  V  D  Q  E  K  K  A  Y  S  F  C  G  T  V  E  Y  239
ATATGGCTCCTGAAGTAGTAAATAGGAGAGGCCATTCCCAGAGTGCTGATTGGTGGTCAT  780
  M  A  P  E  V  V  N  R  R  G  H  S  Q  S  A  D  W  W  S  Y  259
ATGGTGTTCTTATGTTTGAAATGCTTACTGGTACTCTGCCATTTCAAGGTAAAGACAGAA  840
  G  V  L  M  F  E  M  L  T  G  T  L  P  F  Q  G  K  D  R  N  279
ATGAGACCATGAATATGATATTAAAAGCAAAACTTGGAATGCCTCAATTTCTTAGTGCTG  900
  E  T  M  N  M  I  L  K  A  K  L  G  M  P  Q  F  L  S  A  E  299
AAGCACAAAGTCTTCTAAGGATGTTATTCAAAAGGAATCCAGCAAATAGATTGGGATCAG  960
  A  Q  S  L  L  R  M  L  F  K  R  N  P  A  N  R  L  G  S  E  319
AAGGAGTTGAAGAAATCAAAAGACATCTGTTTTTTGCAAATATTGACTGGGATAAATTAT  1020
  G  V  E  E  I  K  R  H  L  F  F  A  N  I  D  W  D  K  L  Y  339
ATAAAAGAGAAGTTCAACCTCCTTTCAAACCTGCTTCTGGAAAACCAGATGATACTTTTT  1080
  K  R  E  V  Q  P  P  F  K  P  A  S  G  K  P  D  D  T  F  C  359
```

Fig. 1b

```
GTTTTGATCCTGAATTTACTGCAAAAACACCTAAAGATTCTCCCGGTTTGCCAGCCAGTG 1140
   F  D  P  E  F  T  A  K  T  P  K  D  S  P  G  L  P  A  S  A 379
CAAATGCTCATCAGCTCTTCAAAGGATTCAGCTTTGTTGCAACTTCTATTGCAGAAGAAT 1200
   N  A  H  Q  L  F  K  G  F  S  F  V  A  T  S  I  A  E  E  Y 399
ATAAAATCACTCCTATCACAAGTGCAAATGTATTACCAATTGTTCAGATAAATGGAAATG 1260
   K  I  T  P  I  T  S  A  N  V  L  P  I  V  Q  I  N  G  N  A 419
CTGCACAATTTGGTGAAGTATATGAATTGAAGGAGGATATTGGTGTTGGCTCCTACTCTG 1320
   A  Q  F  G  E  V  Y  E  L  K  E  D  I  G  V  G  S  Y  S  V 439
TTTGCAAGCGATGCATACATGCAACTACCAACATGGAATTTGCAGTGAAGATCATTGACA 1380
   C  K  R  C  I  H  A  T  T  N  M  E  F  A  V  K  I  I  D  K 459
AAAGTAAGCGAGACCCTTCAGAAGAGATTGAAATATTGATGCGCTATGGACAACATCCCA 1440
   S  K  R  D  P  S  E  E  I  E  I  L  M  R  Y  G  Q  H  P  N 479
ACATTATTACTTTGAAGGATGTCTTTGATGATGGTAGATATGTTTACCTTGTTACGGATT 1500
   I  I  T  L  K  D  V  F  D  D  G  R  Y  V  Y  L  V  T  D  L 499
TAATGAAAGGAGGAGAGTTACTTGACCGTATTCTCAAACAAAAATGTTTCTCGGAACGGG 1560
   M  K  G  G  E  L  L  D  R  I  L  K  Q  K  C  F  S  E  R  E 519
AGGCTAGTGATATACTATATGTAATAAGTAAGACAGTTGACTATCTTCATTGTCAAGGAG 1620
   A  S  D  I  L  Y  V  I  S  K  T  V  D  Y  L  H  C  Q  G  V 539
TTGTTCATCGTGATCTTAAACCTAGTAATATTTTATACATGGATGAATCAGCCAGTGCAG 1680
   V  H  R  D  L  K  P  S  N  I  L  Y  M  D  E  S  A  S  A  D 559
ATTCAATCAGGATATGTGATTTTGGGTTTGCAAAACAACTTCGAGGAGAAAATGGACTTC 1740
   S  I  R  I  C  D  F  G  F  A  K  Q  L  R  G  E  N  G  L  L 579
TCTTAACTCCATGCTACACTGCAAACTTTGTTGCACCTGAGGTTCTTATGCAACAGGGAT 1800
   L  T  P  C  Y  T  A  N  F  V  A  P  E  V  L  M  Q  Q  G  Y 599
ATGATGCTGCTTGTGATATCTGGAGTTTAGGAGTCCTTTTTTACACAATGTTGGCTGGCT 1860
   D  A  A  C  D  I  W  S  L  G  V  L  F  Y  T  M  L  A  G  Y 619
ACACTCCATTTGCTAATGGCCCCAATGATACTCCTGAAGAGATACTGCTGCGTATAGGCA 1920
   T  P  F  A  N  G  P  N  D  T  P  E  E  I  L  L  R  I  G  N 639
ATGGAAAATTCTCTTTGAGTGGTGGAAACTGGGACAATATTTCAGACGGAGCAAAGGGAG 1980
   G  K  F  S  L  S  G  G  N  W  D  N  I  S  D  G  A  K  G  A 659
CAATGGTTGCAACATACTCTGCCCTGACTCACAAGACCTTTCAACCAGTCCTAGAGCCTG 2040
   M  V  A  T  Y  S  A  L  T  H  K  T  F  Q  P  V  L  E  P  V 679
TAGCTGCTTCAAGCTTAGCCCAGCGACGGAGCATGAAAAAGCGAACATCAACTGGCCTGT 2100
   A  A  S  S  L  A  Q  R  R  S  M  K  K  R  T  S  G  L  *    698
AAGATTTGTGGTGTTCCTAGGCCAAACTGGATGAAGATGAAATTAAATGTGTGGCTTTTT 2160
TCCTATTCTTATCAAAGGCATCGTTGTCTGCTAAATTACTTGAATATTAAGTAATATTAA 2220
ATCCCCATTTTTAGGGGAAGTGAGATTTAAAAAACCATTCACAGGTCCACAATATTCATA 2280
```

Fig. 1c

```
CTATGTGTTTGCAGTAGTGTTCAAGTGTTTATTTAAGCATATAATTGGTGTCCACCAGGT 2340
CCTCACAACTTCTCTGCACACAAGCTTCTAAAATTCCTTTCAAATAAAGTTACTTTAATA 2400
TTT                                                          2403
```

Fig. 2a

```
        1
   60
R       P       S       6       K       A       6       V
GGGAAATGCTACCATTCGCTCCTCAGGACGAGCCCTGGGACCGAGAAATGGAAGTGTTCA
R       P       S       6       K       A       6
GGGAAATGCTACCATTCGCTCCTCAGGACGAGCCCTGGGACCGAGAAATGGAAGTGTTCA 61
  120
R       P       S       6       K       A       6       V
GCGGCGGCGGCGCGAGCAGCGGCGAGGTAAATGGTCTTAAAATGGTTGATGAGCCAATGG
R       P       S       6       K       A       6
GCGGCGGCGGCGCGAGCAGCGGCGAGGTAAATGGTCTTAAAATGGTTGATGAGCCAATGG 121
  180
R       P       S       6       K       A       6       V
AAGAGGGAGAAGCAGATTCTTGTCATGATGAAGGAGTTGTTAAAGAAATCCCTATTACTC
R       P       S       6       K       A       6
AAGAGGGAGAAGCAGATTCTTGTCATGATGAAGGAGTTGTTAAAGAAATCCCTATTACTC 181
  240
R       P       S       6       K       A       6       V
ATCATGTTAAGGAAGGCTATGAGAAAGCAGATCCTGCACAGTTTGAGTTGCTCAAGGTTC
R       P       S       6       K       A       6
ATCATGTTAAGGAAGGCTATGAGAAAGCAGATCCTGCACAGTTTGAGTTGCTCAAGGTTC 241
  300
R       P       S       6       K       A       6       V
TTGGTCAGGGGTCATTTGGAAAGGTTTTTCTTGTTAGAAAGAAGACCGGTCCTGATGCTG
R       P       S       6       K       A       6
TTGGTCAGGGGTCATTTGGAAAGGTTTTTCTTGTTAGAAAGAAGACCGGTCCTGATGCTG 301
  360
R       P       S       6       K       A       6       V
GGCAGCTCTATGCAATGAAGGTGTTAAAAAAGCCTCTTTAAAAGTTCGAGACAGAGTTC
RPS6KA6
```

Fig. 2b

```
GGCAGCTCTATGCAATGAAGGTGTTAAAAAAAGCCTCTTTAAAAGTTCGAGACAGAGTTC 361
   420
R        P        S        6        K        A        6        V
GGACAAAGATGGAGAGGGATATACTGGTGGAAGTAAATCATCCATTTATTGTCAAATTGC
R        P        S        6        K        A        6
GGACAAAGATGGAGAGGGATATACTGGTGGAAGTAAATCATCCATTTATTGTCAAATTGC 421
   480
R        P        S        6        K        A        6        V
ACTATGCCTTTCAGACTGAAGGGAAACTGTACTTAATACTGGATTTTCTCAGGGGAGGAG
R        P        S        6        K        A        6
ACTATGCCTTTCAGACTGAAGGGAAACTGTACTTAATACTGGATTTTCTCAGGGGAGGAG 481
   540
R        P        S        6        K        A        6        V
ATGTTTTCACAAGATTATCCAAAGAGGTTCTGTTTACAGAGGAAGATGTGAAATTCTACC
R        P        S        6        K        A        6
ATGTTTTCACAAGATTATCCAAAGAGGTTCTGTTTACAGAGGAAGATGTGAAATTCTACC 541
   600
R        P        S        6        K        A        6        V
TCGCAGAACTGGCCCTTGCTTTGGATCATCTGCACCAATTAGGAATTGTTTATAGAGACC
R        P        S        6        K        A        6
TCGCAGAACTGGCCCTTGCTTTGGATCATCTGCACCAATTAGGAATTGTTTATAGAGACC 601
   660
R        P        S        6        K        A        6        V
TGAAGCCAGAAAACATTTTGCTTGATGAAATAGGACATATCAAATTAACAGATTTTGGAC
R        P        S        6        K        A        6
TGAAGCCAGAAAACATTTTGCTTGATGAAATAGGACATATCAAATTAACAGATTTTGGAC
```

Fig. 2c

```
R        P        S        6        K        A        6        V
TCAGCAAGGAGTCAGTAGATCAAGAAAAGAAGGCTTACTCATTTTGTGGTACAGTAGAGT
R        P        S        6        K        A                 6
TCAGCAAGGAGTCAGTAGATCAAGAAAAGAAGGCTTACTCATTTTGTGGTACAGTAGAGT 721
   780
R        P        S        6        K        A        6        V
ATATGGCTCCTGAAGTAGTAAATAGGAGAGGCCATTCCCAGAGTGCTGATTGGTGGTCAT
R        P        S        6        K        A                 6
ATATGGCTCCTGAAGTAGTAAATAGGAGAGGCCATTCCCAGAGTGCTGATTGGTGGTCAT 781
   840
R        P        S        6        K        A        6        V
ATGGTGTTCTTATGTTTGAAATGCTTACTGGTACTCTGCCATTTCAAGGTAAAGACAGAA
R        P        S        6        K        A                 6
ATGGTGTTCTTATGTTTGAAATGCTTACTGGTACTCTGCCATTTCAAGGTAAAGACAGAA 841
   900
R        P        S        6        K        A        6        V
ATGAGACCATGAATATGATATTAAAAGCAAAACTTGGAATGCCTCAATTTCTTAGTGCTG
R        P        S        6        K        A                 6
ATGAGACCATGAATATGATATTAAAAGCAAAACTTGGAATGCCTCAATTTCTTAGTGCTG 901
   960
R        P        S        6        K        A        6        V
AAGCACAAAGTCTTCTAAGGATGTTATTCAAAAGGAATCCAGCAAATAGATTGGGATCAG
R        P        S        6        K        A                 6
AAGCACAAAGTCTTCTAAGGATGTTATTCAAAAGGAATCCAGCAAATAGATTGGGATCAG 961
  1020
R        P        S        6        K        A        6        V
AAGGAGTTGAAGAAATCAAAAGACATCTGTTTTTTGCAAATATTGACTGGGATAAATTAT
R        P        S        6        K        A                 6
AAGGAGTTGAAGAAATCAAAAGACATCTGTTTTTTGCAAATATTGACTGGGATAAATTAT
```

Fig. 2d

```
        1021
1080
R       P       S       6       K       A       6       V
ATAAAAGAGAAGTTCAACCTCCTTTCAAACCTGCTTCTGGAAAACCAGATGATACTTTTT
R       P       S       6       K       A       6
ATAAAAGAGAAGTTCAACCTCCTTTCAAACCTGCTTCTGGAAAACCAGATGATACTTTTT 1081
1140
R       P       S       6       K       A       6       V
GTTTTGATCCTGAATTTACTGCAAAAACACCTAAAGATTCTCCCGGTTTGCCAGCCAGTG
R       P       S       6       K       A       6
GTTTTGATCCTGAATTTACTGCAAAAACACCTAAAGATTCTCCCGGTTTGCCAGCCAGTG 1141
1200
R       P       S       6       K       A       6       V
CAAATGCTCATCAGCTCTTCAAAGGATTCAGCTTTGTTGCAACTTCTATTGCAGAAGAAT
R       P       S       6       K       A       6
CAAATGCTCATCAGCTCTTCAAAGGATTCAGCTTTGTTGCAACTTCTATTGCAGAAGAAT 1201
1260
R       P       S       6       K       A       6       V
ATAAAATCACTCCTATCACAAGTGCAAATGTATTACCAATTGTTCAGATAAATGGAAATG
R       P       S       6       K       A       6
ATAAAATCACTCCTATCACAAGTGCAAATGTATTACCAATTGTTCAGATAAATGGAAATG 1261
1320
R       P       S       6       K       A       6       V
CTGCACAATTTGGTGAAGTATATGAATTGAAGGAGGATATTGGTGTTGGCTCCTACTCTG
R       P       S       6       K       A       6
CTGCACAATTTGGTGAAGTATATGAATTGAAGGAGGATATTGGTGTTGGCTCCTACTCTG 1321
1380
```

Fig. 2e

```
R         P         S         6         K         A         6         V
TTTGCAAGCGATGCATACATGCAACTACCAACATGGAATTTGCAGTGAAGATCATTGACA
R         P         S         6         K         A                   6
TTTGCAAGCGATGCATACATGCAACTACCAACATGGAATTTGCAGTGAAGATCATTGACA 1381
1440
R         P         S         6         K         A         6         V
AAAGTAAGCGAGACCCTTCAGAAGAGATTGAAATATTGATGCGCTATGGACAACATCCCA
R         P         S         6         K         A                   6
AAAGTAAGCGAGACCCTTCAGAAGAGATTGAAATATTGATGCGCTATGGACAACATCCCA 1441
1500
R         P         S         6         K         A         6         V
ACATTATTACTTTGAAGGATGTCTTTGATGATGGTAGATATGTTTACCTTGTTACGGATT
R         P.        S         6         K         A                   6
ACATTATTACTTTGAAGGATGTCTTTGATGATGGTAGATATGTTTACCTTGTTACGGATT 1501
1560
R         P         S         6         K         A         6         V
TAATGAAAGGAGGAGAGTTACTTGACCGTATTCTCAAACAAAAATGTTTCTCGGAACGGG
R         P         S         6         K         A                   6
TAATGAAAGGAGGAGAGTTACTTGACCGTATTCTCAAACAAAAATGTTTCTCGGAACGGG 1561
1620
R         P         S         6         K         A         6         V
AGGCTAGTGATATACTATATGTAATAAGTAAGACAGTTGACTATCTTCATTGTCAAGGAG
R         P         S         6         K         A                   6
AGGCTAGTGATATACTATATGTAATAAGTAAGACAGTTGACTATCTTCATTGTCAAGGAG 1621
1680
R         P         S         6         K         A         6         V
TTGTTCATCGTGATCTTAAACCTAGTAATATTTTATACATGGATGAATCAGCCAGTGCAG
```

Fig. 2f

```
R          P          S          6          K          A          6
TTGTTCATCGTGATCTTAAACCTAGTAATATTTTATACATGGATGAATCAGCCAGTGCAG 1681                                                    1740
R          P          S          6          K          A          6         V
ATTCAATCAGGATATGTGATTTTGGGTTTGCAAAACAACTTCGAGGAGAAAATGGACTTC
R          P          S          6          K          A          6
ATTCAATCAGGATATGTGATTTTGGGTTTGCAAAACAACTTCGAGGAGAAAATGGACTTC 1741                                                    1800
R          P          S          6          K          A          6         V
TCTTAACTCCATGCTACACTGCAAACTTTGTTGCACCTGAGGTTCTTATGCAACAGGGAT
R          P          S          6          K          A          6
TCTTAACTCCATGCTACACTGCAAACTTTGTTGCACCTGAGGTTCTTATGCAACAGGGAT 1801                                                    1860
R          P          S          6          K          A          6         V
ATGATGCTGCTTGTGATATCTGGAGTTTAGGAGTCCTTTTTTACACAATGTTGGCTGGCT
R          P          S          6          K          A          6
ATGATGCTGCTTGTGATATCTGGAGTTTAGGAGTCCTTTTTTACACAATGTTGGCTGGCT 1861                                                    1920
R          P          S          6          K          A          6         V
ACACTCCATTTGCTAATGGCCCCAATGATACTCCTGAAGAGATACTGCTGCGTATAGGCA
R          P          S          6          K          A          6
ACACTCCATTTGCTAATGGCCCCAATGATACTCCTGAAGAGATACTGCTGCGTATAGGCA 1921                                                    1980
R          P          S          6          K          A          6         V
ATGGAAAATTCTCTTTGAGTGGTGGAAACTGGGACAATATTTCAGACGGAGCAAAGG---
R          P          S          6          K          A          6
ATGGAAAATTCTCTTTGAGTGGTGGAAACTGGGACAATATTTCAGACGGAGCAAAGGATT

```
       2040
RPS6KA6V ------------------------------------------------
----
R         P         S         6        K       A        6
TGCTTTCCCATATGCTTCATATGGACCCACATCAGCGGTATACTGCTGAACAAATATTAA 2041
2100
·RPS6KA6V ------------------------------------------------
----
R         P         S         6        K       A        6
AGCACTCATGGATAACTCACAGAGACCAGTTGCCAAATGATCAGCCAAAGAGAAATGATG 2101
2160
R P S 6 K A 6 V       - - - - - - - - - - - - - - - - - -
GAGCAATGGTTGCAACATACTCTGCCCTGACTCACAAGACCT
R         P         S         6        K       A        6
TGTCACATGTTGTTAAGGGAGCAATGGTTGCAACATACTCTGCCCTGACTCACAAGACCT

Page 25.1
         2161
2220
R         P         S         6        K       A        6       V
TTCAACCAGTCCTAGAGCCTGTAGCTGCTTCAAGCTTAGCCCAGCGACGGAGCATGAAAA
R         P         S         6        K       A        6
TTCAACCAGTCCTAGAGCCTGTAGCTGCTTCAAGCTTAGCCCAGCGACGGAGCATGAAAA 2221
2280
R         P         S         6        K       A        6       V
AGCGAACATCAACTGGCCTGTAAGATTTGTGGTGTTCCTAGGCCAAACTGGATGAAGATG
R         P         S         6        K       A        6
AGCGAACATCAACTGGCCTGTAAGATTTGTGGTGTTCCTAGGCCAAACTGGATGAAGATG 2281
2340
```

Fig. 2h

```
R         P         S         6         K         A         6         V
AAATTAAATGTGTGGCTTTTTTCCTATTCTTATCAAAGGCATCGTTGTCTGCTAAATTAC
R         P         S         6         K         A         6
AAATTAAATGTGTGGCTTTTTTCCTATTCTTATCAAAGGCATCGTTGTCTGCTAAATTAC
                    2341
2400
R         P         S         6         K         A         6         V
TTGAATATTAAGTAATATTAAATCCCCATTTTTAGGGGAAGTGAGATTTAAAAAACCATT
R         P         S         6         K         A         6
TTGAATATTAAGTAATATTAAATCCCCATTTTTAGGGGAAGTGAGATTTAAAAAACCATT
                    2401
2460
R         P         S         6         K         A         6         V
CACAGGTCCACAATATTCATACTATGTGTTTGCAGTAGTGTTCAAGTGTTTATTTAAGCA
R         P         S         6         K         A         6
CACAGGTCCACAATATTCATACTATGTGTTTGCAGTAGTGTTCAAGTGTTTATTTAAGCA
                    2461
2520
R         P         S         6         K         A         6         V
TATAATTGGTGTCCACCAGGTCCTCACAACTTCTCTGCACACAAGCTTCTAAAATTCCTT
R         P         S         6         K         A         6
TATAATTGGTGTCCACCAGGTCCTCACAACTTCTCTGCACACAAGCTTCTAAAATTCCTT
                    2521
RPS6KA6V    TCAAATAAAGTTACTTTAATATTT    2403
RPS6KA6     TCAAATAAAGTTACTTTAATATTT    2544
```

Fig. 3a

```
        1
  60
R         P         S         6         K         A         6         V
MLPFAPQDEPWDREMEVFSGGGASSGEVNGLKMVDEPMEEGEADSCHDEGVVKEIPITHH
R         P         S         6         K         A         6
MLPFAPQDEPWDREMEVFSGGGASSGEVNGLKMVDEPMEEGEADSCHDEGVVKEIPITHH 61
  120
R         P         S         6         K         A         6         V
VKEGYEKADPAQFELLKVLGQGSFGKVFLVRKKTGPDAGQLYAMKVLKKASLKVRDRVRT
R         P         S         6         K         A         6
VKEGYEKADPAQFELLKVLGQGSFGKVFLVRKKTGPDAGQLYAMKVLKKASLKVRDRVRT 121
  180
R         P         S         6         K         A         6         V
KMERDILVEVNHPFIVKLHYAFQTEGKLYLILDFLRGGDVFTRLSKEVLFTEEDVKFYLA
R         P         S         6         K         A         6
KMERDILVEVNHPFIVKLHYAFQTEGKLYLILDFLRGGDVFTRLSKEVLFTEEDVKFYLA 181
  240
R         P         S         6         K         A         6         V
ELALALDHLHQLGIVYRDLKPENILLDEIGHIKLTDFGLSKESVDQEKKAYSFCGTVEYM
R         P         S         6         K         A         6
ELALALDHLHQLGIVYRDLKPENILLDEIGHIKLTDFGLSKESVDQEKKAYSFCGTVEYM 241
  300
R         P         S         6         K         A         6         V
APEVVNRRGHSQSADWWSYGVLMFEMLTGTLPFQGKDRNETMNMILKAKLGMPQFLSAEA
R         P         S         6         K         A         6
APEVVNRRGHSQSADWWSYGVLMFEMLTGTLPFQGKDRNETMNMILKAKLGMPQFLSAEA 301
  360
R         P         S         6         K         A         6         V
QSLLRMLFKRNPANRLGSEGVEEIKRHLFFANIDWDKLYKREVQPPFKPASGKPDDTFCF
```

Fig. 3b

```
R         P        S        6         K         A          6
QSLLRMLFKRNPANRLGSEGVEEIKRHLFFANIDWDKLYKREVQPPFKPASGKPDDTFCF 361
   420
R         P        S        6         K         A          6        V
DPEFTAKTPKDSPGLPASANAHQLFKGFSFVATSIAEEYKITPITSANVLPIVQINGNAA
R         P        S        6         K         A          6
DPEFTAKTPKDSPGLPASANAHQLFKGFSFVATSIAEEYKITPITSANVLPIVQINGNAA 421
   480
R         P        S        6         K         A          6        V
QFGEVYELKEDIGVGSYSVCKRCIHATTNMEFAVKIIDKSKRDPSEEIEILMRYGQHPNI
R         P        S        6         K         A          6
QFGEVYELKEDIGVGSYSVCKRCIHATTNMEFAVKIIDKSKRDPSEEIEILMRYGQHPNI 481
   540
R         P        S        6         K         A          6        V
ITLKDVFDDGRYVYLVTDLMKGGELLDRILKQKCFSEREASDILYVISKTVDYLHCQGVV
R         P        S        6         K         A          6
ITLKDVFDDGRYVYLVTDLMKGGELLDRILKQKCFSEREASDILYVISKTVDYLHCQGVV 541
   600
R         P        S        6         K         A          6        V
HRDLKPSNILYMDESASADSIRICDFGFAKQLRGENGLLLTPCYTANFVAPEVLMQQGYD
R         P        S        6         K         A          6
HRDLKPSNILYMDESASADSIRICDFGFAKQLRGENGLLLTPCYTANFVAPEVLMQQGYD 601
   660
R         P        S        6         K         A          6        V
AACDIWSLGVLFYTMLAGYTPFANGPNDTPEEILLRIGNGKFSLSGGNWDNISDGAK---
R         P        S        6         K         A          6
AACDIWSLGVLFYTMLAGYTPFANGPNDTPEEILLRIGNGKFSLSGGNWDNISDGAKDLL

661
```

HUMAN RPS6KA6-RELATED GENE VARIANT ASSOCIATED WITH LUNG CANCERS

This application is a continuation-in-part of copending application Ser. No. 10/102,554 filed on Mar. 20, 2002 now abandoned.

FIELD OF THE INVENTION

The invention relates to the nucleic acid and polypeptide sequences of a novel human RPS6KA6-related gene variant, the preparation process thereof, and the uses of the same in diagnosing cancers, in particular, T-cell lymphoblastic lymphoma.

BACKGROUND OF THE INVENTION

Lymphoma is the third most common cancer among children in the world. The major types of lymphoma are Hodgkin's and non-Hodgkin's. Non-Hodgkin's lymphoma (NHL) occurs more frequently than Hodgkin's disease among children. The major histopathological categories of NHL in children are (1) Burkitt's and Burkitt's like lymphomas; (2) lymphoblastic lymphomas; (3) anaplastic large cell lymphoma; and (4) diffuse large cell lymphomas (Percy et al., 1999). In recent years, much progress has been made toward understanding the molecular and cellular biology of NHL. Many important contributions have been made by the characteristics of chromosal translocations and identification of several key genetic factors associated with each type of NHL (Percy et al., 1999). However, the treatments of NHL still mainly depend on chemotherapy and radiotherapy. This is because the molecular mechanisms underlying the pathogenesis of NHL remain largely unclear.

Lymphoblastic lymphoma, a predominant T-cell tumor, accounts for about 30% of childhood NHL (National Cancer Institute Cancer.gov Web site, 2004). Recent studies have shown that T cell lymphoblastic lymphoma is caused by abnormal expression of several genetic factors such as BCL-6 (Hyjek et al., (2001) Blood. 97: 270–276), MSH2/Lmo-2Tal-1 (Lowsky et al., (1997) Blood. 89: 2276–2282) and Stat5 (Kelly et al., (2003) J Exp Med. 198: 79–89). Stat5 has been shown to play a role in cell cycle regulation (Nieborowska-Skorska et al., (1999) J Exp Med. 189: 1229–1242; Martino et al., (2001) J Immunol. 166: 1723–1729). Therefore, future strategies for the prevention and treatment of T cell lymphoblastic lymphoma will focus on the elucidation of genetic substances associated with cell cycle regulation. Interestingly, three members (RSK1, RSK2, and RSK3) of the ribosomal S6 kinase (RSK) family have been shown to be involved in the cell cycle regulation and may play a role in T cell (Edelmann et al., (1996) J Biol chem. 271: 963–71; Zhao et al., (1996) J Biol Chem. 271: 29773–29779; Brennan et al., (1999) Mol Cell Biol. 19:4729–38; Suzuki et al., (2001) J Immunol. 167:3064–73). Thus, it raised a possibility that RPS6KA6 (ribosomal S6 kinase 4; also named RSK4; GenBank accession # AF184965) has a role in the development of T cell lymphoblastic lymphoma. Therefore, the discovery of gene variants of RPS6KA6 may be important targets for diagnostic markers of T cell lymphoblastic lymphoma.

SUMMARY OF THE INVENTION

The present invention provides an RPS6KA6-related gene variant (RPS6KA6V) which is negatively expressed in human T cell lymphoblastic lymphoma. The nucleotide sequence of the gene variant and the polypeptide sequence encoded thereby can be used for the diagnosis of any diseases associated with the gene variant or T cell lymphoblastic lymphoma.

The invention further provides an expression vector and host cell for expressing the variant.

The invention further provides a method for producing the variant.

The invention further provides an antibody specifically binding to the variant.

The invention also provides methods for detecting the presence of the variant in a mammal.

BRIEF DESCRIPTION OF THE DRAWINGS

FIG. 1 shows the nucleic acid sequence (SEQ ID NO: 1) and amino acid sequence (SEQ ID NO: 2) of RPS6KA6V.

FIG. 2 shows the nucleotide sequence alignment between the human RPS6KA6 gene (SEQ ID NO: 3) and its related gene variant (RPS6KA6V).

FIG. 3 shows the amino acid sequence alignment between the human RPS6KA6 protein (SEQ ID NO: 4) and its related gene variant (RPS6KA6V).

DETAILED DESCRIPTION OF THE INVENTION

Figure 4:
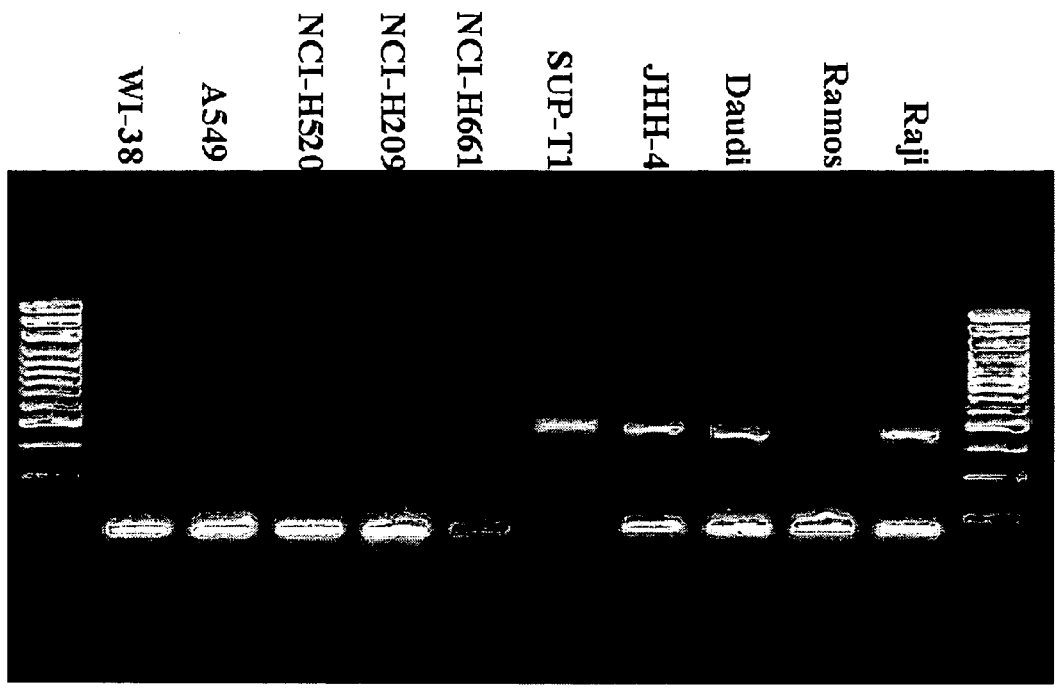
FIG. 4 shows the semi-quantitative RT-PCR analysis of RPS6KA6V in human cell lines, wherein the left and right columns are 100 bp DNA markers.

According to the present invention, all technical and scientific terms used have the same meanings as commonly understood by persons skilled in the art.

The term "antibody" used herein denotes intact molecules (a polypeptide or group of polypeptides) as well as fragments thereof, such as Fab, R(ab')$_2$, and Fv fragments, which are capable of binding the epitopic determinant. Antibodies are produced by specialized B cells after stimulation by an antigen. Structurally, antibody consists of four subunits including two heavy chains and two light chains. The internal surface shape and charge distribution of the antibody binding domain is complementary to the features of an antigen. Thus, antibody can specifically act against the antigen in an immune response.

The term "base pair (bp)" used herein denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool (BLAST; Altschul et al., (1997) Nucleic Acids Res. 25: 3389–3402)" used herein denotes programs for evaluation of homologies between a query sequence (amino or nucleic acid) and a test sequence as described by Altschul et al. (Nucleic Acids Res. 25: 3389–3402, 1997). Specific BLAST programs are described as follows:

(1) BLASTN compares a nucleotide query sequence with a nucleotide sequence database;

(2) BLASTP compares an amino acid query sequence with a protein sequence database;

(3) BLASTX compares the six-frame conceptual translation products of a query nucleotide sequence with a protein sequence database;

(4) TBLASTN compares a query protein sequence with a nucleotide sequence database translated in all six reading frames; and (5) TBLASTX compares the six-frame translations of a nucleotide query sequence with the six-frame translations of a nucleotide sequence database.

The term "cDNA" used herein denotes nucleic acids that synthesized from a mRNA template using reverse transcriptase.

The term "cDNA library" used herein denotes a library composed of complementary DNAs, which are reverse-transcribed from mRNAs.

The term "complement" used herein denotes a polynucleotide sequence capable of forming base pairing with another polynucleotide sequence. For example, the sequence 5'-ATGGACTTACT-3' binds to the complementary sequence 5'-AGTAAGTCCAT-3'.

The term "deletion" used herein denotes a removal of a portion of one or more amino acid residues/nucleotides from a gene.

The term "expressed sequence tags (ESTs)" used herein denotes short (200 to 500 base pairs) nucleotide sequence derived from either 5' or 3' end of a cDNA.

The term "expression vector" used herein denotes nucleic acid constructs which contain a cloning site for introducing the DNA into vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell" used herein denotes a cell, which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition" used herein denotes the addition of a portion of one or more amino acid residues/nucleotides to a gene.

The term "in silico" used herein denotes a process of using computational methods (e.g., BLAST) to analyze DNA sequences.

The term "polymerase chain reaction (PCR)" used herein denotes a method which increases the copy number of a nucleic acid sequence using a DNA polymerase and a set of primers (about 20 bp oligonucleotides complementary to each strand of DNA) under suitable conditions (successive rounds of primer annealing, strand elongation, and dissociation).

The term "protein" or "polypeptide" used herein denotes a sequence of amino acids in a specific order that can be encoded by a gene or by a recombinant DNA. It can also be chemically synthesized.

The term "nucleic acid sequence" or "polynucleotide" used herein denotes a sequence of nucleotide (guanine, cytosine, thymine or adenine) in a specific order that can be a natural or synthesized fragment of DNA or RNA. It may be single-stranded or double-stranded.

The term "reverse transcriptase-polymerase chain reaction (RT-PCR)" used herein denotes a process which transcribes mRNA to complementary DNA strand using reverse transcriptase followed by polymerase chain reaction to amplify the specific fragment of DNA sequences.

The term "transformation" used herein denotes a process describing the uptake, incorporation, and expression of exogenous DNA by prokaryotic host cells.

The term "transfection" used herein denotes a process describing the uptake, incorporation, and expression of exogenous DNA by eukaryotic host cells.

The term "variant" used herein denotes a fragment of sequence (nucleotide or amino acid) inserted or deleted by one or more nucleotides/amino acids.

The present invention provides the polypeptides of a novel human RPS6KA6-related gene variant, as well as the nucleic acid sequences encoding the same.

According to the present invention, human RPS6KA6 cDNA sequence was used to query the human lung EST databases (a normal lung, a large cell lung cancer, a squamous cell lung cancer and a small cell lung cancer) using BLAST program to search for RPS6KA6-related gene variants. Four ESTs showing similarity to RPS6KA6 were identified. Two were from the large cell lung cancer, one was from the squamous cell lung cancer and one was from the SCLC databases. Their corresponding cDNA clones were found to be identical after sequencing and named RPS6KA6V (RPS6KA6 variant). FIG. 1 shows the nucleic acid sequence of RPS6KA6V (SEQ ID NO: 1) and the amino acid sequence encoded thereby (SEQ ID NO: 2).

The full-length of the RPS6KA6V cDNA is a 2403 bp clone containing a 2094 bp open reading frame (ORF) extending from 6 bp to 2099 bp, which corresponds to an encoded protein of 698 amino acid residues with a predicted molecular mass of 78.2 kDa. To determine the variation in sequence of RPS6KA6V cDNA clone, an alignment of RPS6KA6 nucleotide/amino acid sequence with RPS6KA6V was performed (FIGS. 2 and 3). The results indicate that one major genetic deletion was found in the aligned sequences showing that RPS6KA6V is a 141 bp deletion in the sequence of RPS6KA6 from 1978–2118 bp. The lack of 141 bp (corresponding to 47aa) is an in-frame deletion in the amino acid sequence of RPS6KA6 and generates a polypeptide of 698 amino acid residues of RPS6KA6V (FIG. 3).

In the present invention, a search of ESTs deposited in dbEST (Boguski et al. (1993) Nat Genet. 4: 332–3) at NCBI was performed to determine the tissue distribution of RPS6KA6V in silico. The result of in silico Northern analysis showed that one EST (GenBank accession number AA626690) was found to confirm the absence of 141 bp region on RPS6KA6V nucleotide sequence. This EST was also generated from a lung carcinoma cDNA library suggesting that the absence of 141 bp nucleotide fragment located between 1977–1978 bp of RPS6KA6V may serve as a useful marker for diagnosing cancers associated with this gene variant. Therefore, any nucleotide fragments comprising 1977–1978 bp of RPS6KA6V may be used as probes for determining the presence of RPS6KA6V under high stringency conditions. An alternative approach is that any set of primers for amplifying the fragment containing 1977–1978 bp of RPS6KA6V may be used for determining the presence of the variant.

According to the present invention, the polypeptides of the human RPS6KA6V may be produced through genetic engineering techniques. In this case, they are produced by appropriate host cells, which have been transformed by DNAs that code for the polypeptides. The nucleotide sequence encoding the polypeptide containing 657–658aa of the human RPS6KA6V is inserted into an appropriate expression vector, i.e., a vector which contains the necessary elements for the transcription and translation of the inserted coding sequence in a suitable host. The nucleic acid sequence is inserted into the vector in a manner that it will be expressed under appropriate conditions (e.g., in proper orientation and correct reading frame and with appropriate expression sequences, including an RNA polymerase binding sequence and a ribosomal binding sequence).

Any method that is known to those skilled in the art may be used to construct expression vectors containing sequences encoding the polypeptide of the human RPS6KA6V and appropriate transcriptional/translational control elements. These methods may include in vitro recombinant DNA and synthetic techniques, and in vivo genetic recombinants. (See, e.g., Sambrook, J. Cold Spring Harbor Press, Plainview N.Y., ch. 4, 8, and 16–17; Ausubel, R. M. et al. (1995) Current protocols in Molecular Biology, John Wiley & Sons, New York N.Y., ch. 9, 13, and 16.)

A variety of expression vector/host systems may be utilized to express the polypeptide-coding sequence. These include, but not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and most preferably, the bacterium is *E. coli*.

Alternatively, the polypeptide of the human RPS6KA6V or the fragments thereof may be synthesized by using chemical methods. For example, peptide synthesis can be performed using various solid-phase techniques (Roberge, J. Y. et al. (1995) Science 269: 202 to 204). Automated synthesis may be achieved by using the ABI 431A peptide synthesizer (Perkin-Elmer).

According to the present invention, the polypeptide and nucleic acid sequence of the human RPS6KA6V can be used as immunogen and template of primers/or probes, respectively.

The present invention further provides the antibodies which specifically bind one or more out-surface epitopes of the polypeptides of the human RPS6KA6V.

According to the present invention, immunization of mammals with immunogens described herein, preferably humans, rabbits, rats, mice, sheep, goats, cows, or horses, is performed following procedures well known to those skilled in the art, for the purpose of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. Nos. 4,271,145 and 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using column chromatography methods well known to those skilled in the art.

According to the present invention, antibody fragments which contain specific binding sites for the polypeptides may also be generated. For example, such fragments include, but are not limited to, F(ab')$_2$ fragments produced by pepsin digestion of the antibody molecule and Fab fragments generated by reducing the disulfide bridges of the F(ab')$_2$ fragments.

The subject invention also provides methods for diagnosing the diseases associated with the human RPS6KA6V or T cell lymphoblastic lymphoma, by the utilization of the nucleic acid sequence, the polypeptide of the human RPS6KA6V, and the antibodies against the polypeptide.

Many gene variants have been found to be associated with diseases (Stallings-Mann et al., (1996) Proc Natl Acad Sci USA 93: 12394–9; Liu et al., (1997) Nat Genet 16:328–9; Siffert et al., (1998) Nat Genet 18: 45 to 8; Lukas et al., (2001) Cancer Res 61: 3212 to 9). Since RPS6KA6V clone was isolated from lung cancers cDNA libraries and identified its expression in lung carcinoma cDNA library using in silico Northern analysis, it is advisable that RPS6KA6V may serve as a marker for the diagnosis of human cancers. Thus, the expression level of RPS6KA6V relative to RPS6KA6 may be a useful indicator for screening of patients suspected of having cancers. This suggests that the index of relative expression level (mRNA or protein) may confer an increased susceptibility to cancers. Fragments of RPS6KA6 mRNA may be detected by RT-PCR approach. Polypeptides of RPS6KA6V may be determined by the binding of antibodies to these polypeptides. These approaches may be performed in accordance with conventional methods well known to persons skilled in the art.

According to the present invention, the expression of the gene variant mRNA in sample may be determined by, but not limited to, RT-PCR. Using TRIZOL reagents (Life Technology), total RNA may be isolated from patient samples. Tissue samples (e.g., biopsy samples) are powdered under liquid nitrogen before homogenization. RNA purity and integrity are assessed by absorbance at 260/280 nm and by agarose gel electrophoresis. A set of primers can be designed to amplify the expected size of specific PCR fragments of RPS6KA6V. For example, one of the primers may be designed to have a sequence comprising the nucleotides of SEQ ID NO: 1 containing nucleotides 1974 to 1979, and the other may be designed to have a sequence complementary to the nucleotides of SEQ ID NO: 1 at any other locations. Alternatively, one of the primers may be designed to have a sequence complementary to the nucleotides of SEQ ID NO: 1 upstream of nucleotide 1977 and the other may be designed to have a sequence comprising the nucleotides of SEQ ID NO: 1 downstream of nucleotide 1978. In this case, both RPS6KA6 and RPS6KA6V will be amplified. The length of the PCR fragment from RPS6KA6V will be 141 bp shorter than that from RPS6KA6. PCR fragments are analyzed on a 1% agarose gel using five microliters (10%) of the amplified products. The intensity of the signals may be determined by using the Molecular Analyst program (version 1.4.1; Bio-Rad). Thus, the index of relative expression levels for each co-amplified PCR product may be calculated based on the intensity of signals.

The RT-PCR experiment may be performed according to the manufacturer's instructions (Boehringer Mannheim). A 50 µl reaction mixture containing 2 µl total RNA (0.1 µg/µl), 1 µl each primer (20 µM), 1 µl each dNTP (10 mM), 2.5 µl DTT solution (100 mM), 10 µl 5×RT-PCR buffer, 1 µl enzyme mixture, and 28.5 µl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

The expression of the gene variant can also be analyzed using Northern Blot hybridization approach. Specific fragment of the RPS6KA6V may be amplified by polymerase chain reaction (PCR) using primer set designed for RT-PCR. The amplified PCR fragment may be labeled and serve as a probe to hybridize the membranes containing total RNAs extracted from the samples under the conditions of 55° C. in a suitable hybridization solution for 3 hr. Blots may be washed twice in 2×SSC, 0.1% SDS at room temperature for 15 minutes each, followed by two washes in 0.1×SSC and 0.1% SDS at 65° C. for 20 minutes each. After these washes, blot may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of gene variant (cDNAs or PCR) can be detected using microarray approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the present invention, the presence of the polypeptide of the gene variant in samples may be determined by, but not limited to, the immunoassay, which uses the antibody specifically binding to the polypeptide. For instance, the polypeptide in protein samples obtained from the mammal suspected of having such diseases may be determined by, but not limited to, the immunoassay wherein the antibody specifically binding to the polypeptide of the invention is brought into contact with the protein samples, and the antibody-polypeptide complex is detected. If necessary, the amount of antibody-polypeptide complex can be determined.

The polypeptides of the human RPS6KA6V may be expressed in prokaryotic cells by using suitable prokaryotic expression vectors. The cDNA fragments of RPS6KA6V gene encoding the amino acid coding sequence may be PCR amplified using primer set with restriction enzyme digestion sites incorporated in the 5' and 3' ends, respectively. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., $E.$ $coli$ BL21 (DE3)). Recombinant protein synthesis may be stimulated by the addition of 0.4 mM isopropylthiogalactoside (IPTG) for 3 h. The bacterially-expressed proteins may be purified.

The polypeptide of the gene variant may be expressed in animal cells by using eukaryotic expression vectors. Cells may be maintained in Dulbecco's modified Eagle's medium (DMEM) supplemented with 10% fetal bovine serum (FBS; Gibco BRL) at 37° C. in a humidified 5% $CO_2$ atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of $5 \times 10^4$ cells per well. Transfections may be carried out using Lipofectamine Plus transfection reagent according to the manufacturer's instructions (Gibco BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins. After these proteins are purified, monoclonal antibodies against these purified proteins (RPS6KA6V) may be generated using hybridoma technique according to the conventional methods (de StGroth and Scheidegger, (1980) J Immunol Methods 35:1–21; Cote et al. (1983) Proc Natl Acad Sci USA 80: 2026–30; and Kozbor et al. (1985) J Immunol Methods 81:31–42).

According to the present invention, the presence of the polypeptides of the gene variant in samples may be determined by, but not limited to, Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 h at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody directed against the polypeptides of gene variants. Unbound antibody is removed by washing with TBST for 5×1 minutes. Bound antibody may be detected using commercial ECL Western blotting detecting reagents.

The following examples are provided for illustration, but not for limiting the invention.

EXAMPLES

Analysis of Human Lung EST Databases

Expressed sequence tags (ESTs) generated from the large-scale PCR-based sequencing of the 5'-end of human lung (normal, SCLC, squamous cell lung cancer and large cell lung cancer) cDNA clones were compiled and served as EST databases. Sequence comparisons against the nonredundant nucleotide and protein databases were performed using BLASTN and BLASTX programs (Altschul et al., (1997) Nucleic Acids Res. 25: 3389–3402; Gish and States, (1993) Nat Genet 3:266–272), at the National Center for Biotechnology Information (NCBI) with a significant cutoff of $p<10^{-10}$. ESTs representing putative RPS6KA6V gene were identified during the course of EST generation.

Isolation of cDNA Clones

Four identical cDNA clones exhibiting EST sequences similar to the RPS6KA6 gene were isolated from lung cancer cDNA libraries and named RPS6KA6V. The inserts of these clones were subsequently excised in vivo from the γZAP Express vector using the ExAssist/XLOLR helper phage system (Stratagene). Phagemid particles were excised by coinfecting XL1-BLUE MRF' cells with ExAssist helper phage. The excised pBluescript phagemids were used to infect E. coli XLOLR cells, which lack the amber suppressor necessary for ExAssist phage replication. Infected XLOLR cells were selected using kanamycin resistance. Resultant colonies contained the double stranded phagemid vector with the cloned cDNA insert. A single colony was grown overnight in LB-kanamycin, and DNA was purified using a Qiagen plasmid purification kit.

Full Length Nucleotide Sequencing and Database Comparisons

Phagemid DNA was sequenced using the Epicentre#SE9101LC SequiTherm EXCEL™II DNA Sequencing Kit for 4200S-2 Global NEW IR$^2$ DNA sequencing system (LI-COR). Using the primer-walking approach, full-length sequence was determined. Nucleotide and protein searches were performed using BLAST against the non-redundant database of NCBI.

In Silico Tissue Distribution (Northern) Analysis

The coding sequence for each cDNA clones was searched against the dbEST sequence database (Boguski et al., (1993) Nat Genet. 4: 332–3) using the BLAST algorithm at the NCBI website. ESTs derived from each tissue were used as a source of information for transcript tissue expression analysis. Tissue distribution for each isolated cDNA clone was determined by ESTs matching to that particular sequence variants (insertions or deletions) with a significance cutoff of $p<10^{-10}$.

Reverse Transcriptase-Polymerase Chain Reaction (RT-PCR) Analysis

Total RNA was extracted from WI-38 (fibroblast), A549 (lung adenocarcinoma), NCI-H661 (lung large cell carcinoma), NCI-H520 (lung squamous carcinoma), NCI-H209 (lung small cell carcinoma), JHH-4 (hepatoma), SUP-T1 (T-cell lymphoblastic lymphoma), Daudi (Burkitt's lymphoma), Ramos (Burkitt's lymphoma), and Raji (Burkitt's lymphoma) cell lines and from four breast cancer, two gastric ulcer, two colon cancer, two hepatoma, one Grave's disease, one colon cancer, one pancreatic carcinoma, one left neck tumor, one gastric carcinoma, two thyroid tumor, one spleen, one pancreatic abscess, one Gastric carcinoma, one adenomatous polyposis, one right neck lymph tissue, one liver cirrhosis, and two parotid gland mixed tumor biopsied samples, RNA purity and is integrity were assessed by the absorbance at 260/280 nm and by agarose gel electrophoresis.

Figure 5:
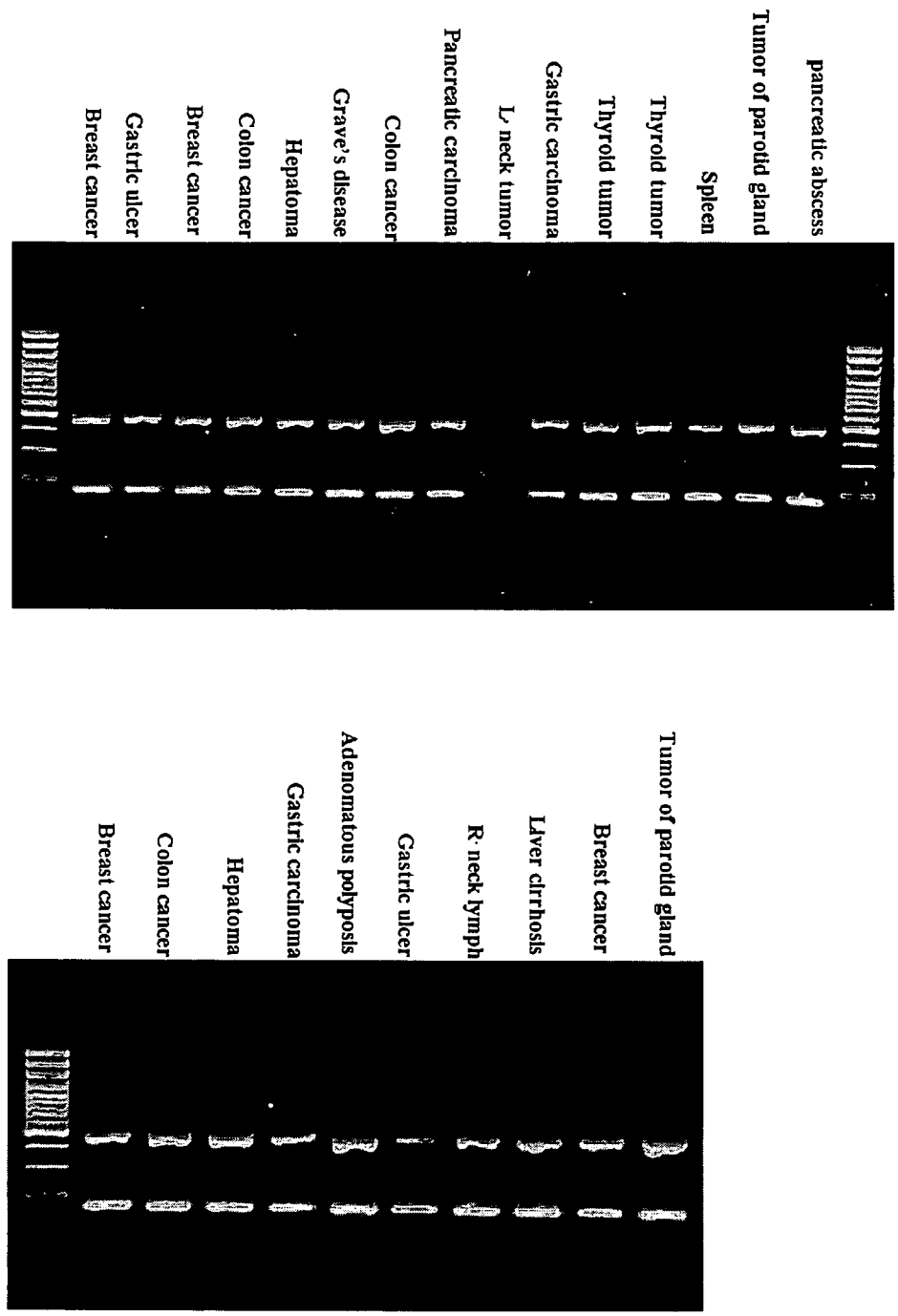
FIG. 5 shows the semi-quantitative RT-PCR analysis of RPS6KA6V in human tissue samples, wherein the left and right columns are 100 bp DNA markers.

The forward and reverse primers for RPS6KA6V were 5'-GGAGCAAAGGGAGCAATGGTTG-3' (SEQ ID NO: 5) and 5'-TCTTCATCCAGTTTGGCCTAGG-3' (SEQ ID NO: 6), respectively. The expected size of the specific PCR fragment was 170 bp. Glyceraldehyde-3-phosphate dehydrogenase (GAPDH; accession No. M33197) was used as an internal control. The forward and reverse primers for GAPDH were 5'-TGGGTGTGAACCATGAGAAG-3' (SEQ ID NO: 7) and 5'-GTGTCGCTGTTGAAGTCAGA-3' (SEQ ID NO: 8), respectively. The expected size of the PCR fragment was 472 bp. The electrophoresis results of the RPS6KA6V mRNA expression patterns in 10 cell lines and 25 biopsied samples determined by RT-PCR are shown in FIGS. 4 and 5. The results showed that RPS6KA6V mRNA was consistently expressed in all cell lines and tissues investigated except in the T-cell lymphoblastic lymphoma cell line. This suggests that RPS6KA6V can be used for diagnosing T-cell lymphoblastic lymphoma when RPS6KA6V mRNA cannot be detected.

REFERENCES

Altschul et al., Gapped BLAST and PSI-BLAST: a new generation of protein database search programs, Nucleic Acids Res, 25: 3389–3402, (1997).

Ausubel et al., Current protocols in Molecular Biology, John Wiley & Sons, New York N.Y., ch. 9, 13, and 16, (1995).

Boguski et al., dbEST—database for "expressed sequence tags". Nat Genet. 4: 332–3, (1993).

Brennan et al., p70(s6k) integrates phosphatidylinositol 3-kinase and rapamycin-regulated signals for E2F regulation in T lymphocytes. Mol Cell Biol. 19:4729–38, (1999).

Cote et al., Generation of human monoclonal antibodies reactive with cellular antigens, Proc Natl Acad Sci USA 80: 2026–30 (1983).

de StGroth and Scheidegger, Production of monoclonal antibodies: strategy and tactics, J Immunol Methods 35:1–21, (1980).

Edelmann et al., Cell cycle regulation of p70 S6 kinase and p42/p44 mitogen-activated protein kinases in Swiss mouse 3T3 fibroblasts. J Biol. Chem. 271: 963–71, (1996).

Frodin and Gammeltoft, Role and regulation of 90 kDa ribosomal S6 kinase (RSK) in signal transduction. Mol Cell Endocrinol, 151:65–77, (1999).

Gish and States, Identification of protein coding regions by database similarity search, Nat Genet, 3:266–272, (1993).

Hyjek et al., BCL-6 protein is expressed in precursor T-cell lymphoblastic lymphoma and in prenatal and postnatal thymus. Blood. 97: 270–276 (2001).

Kelly et al., Stat5 synergizes with T cell receptor/antigen stimulation in the development of lymphoblastic lymphoma. J Exp Med. 198: 79–89, (2003).

Kozbor et al., Specific immunoglobulin production and enhanced tumorigenicity following ascites growth of human hybridomas, J Immunol Methods, 81:31–42 (1985).

Liu et al., Silent mutation induces exon skipping of fibrillin-1 gene in Marfan syndrome. Nat Genet 16:328–9, (1997).

Lowsky et al., Defects of the mismatch repair gene MSH2 are implicated in the development of murine and human lymphoblastic lymphomas and are associated with the aberrant expression of rhombotin-2 (Lmo-2) and Tal-1 (SCL). Blood. 89: 2276–2282, (1997).

Lukas et al., Alternative and aberrant messenger RNA splicing of the mdm2 oncogene in invasive breast cancer. Cancer Res 61:3212–9, (2001).

Martino et al., J. Immunol. Stat5 and Sp1 regulate transcription of the cyclin D2 gene in response to IL-2. 166: 1723–9, (2001).

National Cancer Institute Cancer.gov Web site (http://www.nci.nih.gov/cancerinfo/pdq/treatment/child-non-hodgkins/healthprofessional#Section_1 4). Childhood Non-Hodgkin's Lymphoma (PDQ®): Treatment (Last Modified: Feb. 18, 2004)

Nieborowska-Skorska et al., Signal transducer and activator of transcription (STAT)5 activation by BCR/ABL is dependent on intact Src homology (SH)3 and SH2 domains of BCR/ABL and is required for leukemogenesis. J Exp Med. 189: 1229–1242, (1999).

Percy C L, Smith M A, Linet M, et al.: Lymphomas and reticuloendothelial neoplasms. In: Ries L A, Smith M A, Gurney J G, et al., eds.: Cancer incidence and survival among children and adolescents: United States SEER Program 1975–1995. Bethesda, Md.: National Cancer Institute, SEER Program, 1999. NIH Pub. No. 99-4649. Also available online. Last accessed Sep. 3, 2003, pp 35–50. Last accessed Apr. 21, 2003.

Roberge et al., A strategy for a convergent synthesis of N-linked glycopeptides on a solid support. Science 269: 202–4, (1995).

Sambrook, J. Cold Spring Harbor Press, Plainview N.Y., ch. 4, 8, and 16–17.

Siffert et al., Association of a human G-protein beta3 subunit variant with hypertension. Nat Genet, 18:45–8, (1998).

Stallings-Mann et al., Alternative splicing of exon 3 of the human growth hormone receptor is the result of an unusual genetic polymorphism. Proc Natl Acad Sci USA 93:12394–9, (1996).

Suzuki et al., Diverse transcriptional response of CD4(+) T cells to stromal cell-derived factor (SDF)-1: cell survival promotion and priming effects of SDF-1 on CD4(+) T cells. J. Immunol. 167:3064–73, (2001).

Wilson, R. K. GenBank accession # AA626690

Yntema et al., GenBank accession # AF 184965

Yntema et al., A novel ribosomal S6-kinase (RSK4; RPS6KA6) is commonly deleted in patients with complex X-linked mental retardation. Genomics, 62:332–43, (1999).

Zhao et al., Regulation and interaction of pp90 (rsk) isoforms with mitogen-activated protein kinases. J Biol. Chem. 271: 29773–29779, (1996).

SEQUENCE LISTING

```
<160> NUMBER OF SEQ ID NOS: 8

<210> SEQ ID NO 1
<211> LENGTH: 2403
<212> TYPE: DNA
<213> ORGANISM: Homo sapiens
<220> FEATURE:
<221> NAME/KEY: CDS
<222> LOCATION: (6)..(2099)
<223> OTHER INFORMATION:

<400> SEQUENCE: 1 gggaa atg cta cca ttc gct cct cag gac gag ccc tgg gac cga gaa atg      50
      Met Leu Pro Phe Ala Pro Gln Asp Glu Pro Trp Asp Arg Glu Met
      1               5                  10                  15 gaa gtg ttc agc ggc ggc ggc gcg agc agc ggc gag gta aat ggt ctt        98
Glu Val Phe Ser Gly Gly Gly Ala Ser Ser Gly Glu Val Asn Gly Leu
                 20                  25                  30 aaa atg gtt gat gag cca atg gaa gag gga gaa gca gat tct tgt cat      146
Lys Met Val Asp Glu Pro Met Glu Glu Gly Glu Ala Asp Ser Cys His
             35                  40                  45 gat gaa gga gtt gtt aaa gaa atc cct att act cat cat gtt aag gaa      194
Asp Glu Gly Val Val Lys Glu Ile Pro Ile Thr His His Val Lys Glu
         50                  55                  60 ggc tat gag aaa gca gat cct gca cag ttt gag ttg ctc aag gtt ctt      242
Gly Tyr Glu Lys Ala Asp Pro Ala Gln Phe Glu Leu Leu Lys Val Leu
     65                  70                  75 ggt cag ggg tca ttt gga aag gtt ttt ctt gtt aga aag aag acc ggt      290
Gly Gln Gly Ser Phe Gly Lys Val Phe Leu Val Arg Lys Lys Thr Gly
 80                  85                  90                  95 cct gat gct ggg cag ctc tat gca atg aag gtg tta aaa aaa gcc tct      338
Pro Asp Ala Gly Gln Leu Tyr Ala Met Lys Val Leu Lys Lys Ala Ser
                100                 105                 110 tta aaa gtt cga gac aga gtt cgg aca aag atg gag agg gat ata ctg      386
Leu Lys Val Arg Asp Arg Val Arg Thr Lys Met Glu Arg Asp Ile Leu
            115                 120                 125 gtg gaa gta aat cat cca ttt att gtc aaa ttg cac tat gcc ttt cag      434
Val Glu Val Asn His Pro Phe Ile Val Lys Leu His Tyr Ala Phe Gln
        130                 135                 140
```

-continued

| | |
|---|---|
| act gaa ggg aaa ctg tac tta ata ctg gat ttt ctc agg gga gat<br>Thr Glu Gly Lys Leu Tyr Leu Ile Leu Asp Phe Leu Arg Gly Gly Asp<br>145                            150                        155 | 482 |
| gtt ttc aca aga tta tcc aaa gag gtt ctg ttt aca gag gaa gat gtg<br>Val Phe Thr Arg Leu Ser Lys Glu Val Leu Phe Thr Glu Glu Asp Val<br>160                            165                        170                        175 | 530 |
| aaa ttc tac ctc gca gaa ctg gcc ctt gct ttg gat cat ctg cac caa<br>Lys Phe Tyr Leu Ala Glu Leu Ala Leu Ala Leu Asp His Leu His Gln<br>                        180                        185                        190 | 578 |
| tta gga att gtt tat aga gac ctg aag cca gaa aac att ttg ctt gat<br>Leu Gly Ile Val Tyr Arg Asp Leu Lys Pro Glu Asn Ile Leu Leu Asp<br>                  195                        200                        205 | 626 |
| gaa ata gga cat atc aaa tta aca gat ttt gga ctc agc aag gag tca<br>Glu Ile Gly His Ile Lys Leu Thr Asp Phe Gly Leu Ser Lys Glu Ser<br>                210                        215                        220 | 674 |
| gta gat caa gaa aag aag gct tac tca ttt tgt ggt aca gta gag tat<br>Val Asp Gln Glu Lys Lys Ala Tyr Ser Phe Cys Gly Thr Val Glu Tyr<br>225                            230                        235 | 722 |
| atg gct cct gaa gta gta aat agg aga ggc cat tcc cag agt gct gat<br>Met Ala Pro Glu Val Val Asn Arg Arg Gly His Ser Gln Ser Ala Asp<br>240                            245                        250                        255 | 770 |
| tgg tgg tca tat ggt gtt ctt atg ttt gaa atg ctt act ggt act ctg<br>Trp Trp Ser Tyr Gly Val Leu Met Phe Glu Met Leu Thr Gly Thr Leu<br>                  260                        265                        270 | 818 |
| cca ttt caa ggt aaa gac aga aat gag acc atg aat atg ata tta aaa<br>Pro Phe Gln Gly Lys Asp Arg Asn Glu Thr Met Asn Met Ile Leu Lys<br>                    275                        280                        285 | 866 |
| gca aaa ctt gga atg cct caa ttt ctt agt gct gaa gca caa agt ctt<br>Ala Lys Leu Gly Met Pro Gln Phe Leu Ser Ala Glu Ala Gln Ser Leu<br>                290                        295                        300 | 914 |
| cta agg atg tta ttc aaa agg aat cca gca aat aga ttg gga tca gaa<br>Leu Arg Met Leu Phe Lys Arg Asn Pro Ala Asn Arg Leu Gly Ser Glu<br>305                            310                        315 | 962 |
| gga gtt gaa gaa atc aaa aga cat ctg ttt ttt gca aat att gac tgg<br>Gly Val Glu Glu Ile Lys Arg His Leu Phe Phe Ala Asn Ile Asp Trp<br>320                            325                        330                        335 | 1010 |
| gat aaa tta tat aaa aga gaa gtt caa cct cct ttc aaa cct gct tct<br>Asp Lys Leu Tyr Lys Arg Glu Val Gln Pro Pro Phe Lys Pro Ala Ser<br>                    340                        345                        350 | 1058 |
| gga aaa cca gat gat act ttt tgt ttt gat cct gaa ttt act gca aaa<br>Gly Lys Pro Asp Asp Thr Phe Cys Phe Asp Pro Glu Phe Thr Ala Lys<br>                355                        360                        365 | 1106 |
| aca cct aaa gat tct ccc ggt ttg cca gcc agt gca aat gct cat cag<br>Thr Pro Lys Asp Ser Pro Gly Leu Pro Ala Ser Ala Asn Ala His Gln<br>                370                        375                        380 | 1154 |
| ctc ttc aaa gga ttc agc ttt gtt gca act tct att gca gaa gaa tat<br>Leu Phe Lys Gly Phe Ser Phe Val Ala Thr Ser Ile Ala Glu Glu Tyr<br>385                            390                        395 | 1202 |
| aaa atc act cct atc aca agt gca aat gta tta cca att gtt cag ata<br>Lys Ile Thr Pro Ile Thr Ser Ala Asn Val Leu Pro Ile Val Gln Ile<br>400                            405                        410                        415 | 1250 |
| aat gga aat gct gca caa ttt ggt gaa gta tat gaa ttg aag gag gat<br>Asn Gly Asn Ala Ala Gln Phe Gly Glu Val Tyr Glu Leu Lys Glu Asp<br>                    420                        425                        430 | 1298 |
| att ggt gtt ggc tcc tac tct gtt tgc aag cga tgc ata cat gca act<br>Ile Gly Val Gly Ser Tyr Ser Val Cys Lys Arg Cys Ile His Ala Thr<br>                435                        440                        445 | 1346 |
| acc aac atg gaa ttt gca gtg aag atc att gac aaa agt aag cga gac<br>Thr Asn Met Glu Phe Ala Val Lys Ile Ile Asp Lys Ser Lys Arg Asp<br>                450                        455                        460 | 1394 |

```
cct tca gaa gag att gaa ata ttg atg cgc tat gga caa cat ccc aac    1442
Pro Ser Glu Glu Ile Glu Ile Leu Met Arg Tyr Gly Gln His Pro Asn
    465                 470                 475 att att act ttg aag gat gtc ttt gat gat ggt aga tat gtt tac ctt    1490
Ile Ile Thr Leu Lys Asp Val Phe Asp Asp Gly Arg Tyr Val Tyr Leu
480                 485                 490                 495 gtt acg gat tta atg aaa gga gga gag tta ctt gac cgt att ctc aaa    1538
Val Thr Asp Leu Met Lys Gly Gly Glu Leu Leu Asp Arg Ile Leu Lys
                500                 505                 510 caa aaa tgt ttc tcg gaa cgg gag gct agt gat ata cta tat gta ata    1586
Gln Lys Cys Phe Ser Glu Arg Glu Ala Ser Asp Ile Leu Tyr Val Ile
            515                 520                 525 agt aag aca gtt gac tat ctt cat tgt caa gga gtt gtt cat cgt gat    1634
Ser Lys Thr Val Asp Tyr Leu His Cys Gln Gly Val Val His Arg Asp
        530                 535                 540 ctt aaa cct agt aat att tta tac atg gat gaa tca gcc agt gca gat    1682
Leu Lys Pro Ser Asn Ile Leu Tyr Met Asp Glu Ser Ala Ser Ala Asp
    545                 550                 555 tca atc agg ata tgt gat ttt ggg ttt gca aaa caa ctt cga gga gaa    1730
Ser Ile Arg Ile Cys Asp Phe Gly Phe Ala Lys Gln Leu Arg Gly Glu
560                 565                 570                 575 aat gga ctt ctc tta act cca tgc tac act gca aac ttt gtt gca cct    1778
Asn Gly Leu Leu Leu Thr Pro Cys Tyr Thr Ala Asn Phe Val Ala Pro
                580                 585                 590 gag gtt ctt atg caa cag gga tat gat gct gct tgt gat atc tgg agt    1826
Glu Val Leu Met Gln Gln Gly Tyr Asp Ala Ala Cys Asp Ile Trp Ser
            595                 600                 605 tta gga gtc ctt ttt tac aca atg ttg gct ggc tac act cca ttt gct    1874
Leu Gly Val Leu Phe Tyr Thr Met Leu Ala Gly Tyr Thr Pro Phe Ala
        610                 615                 620 aat ggc ccc aat gat act cct gaa gag ata ctg ctg cgt ata ggc aat    1922
Asn Gly Pro Asn Asp Thr Pro Glu Glu Ile Leu Leu Arg Ile Gly Asn
    625                 630                 635 gga aaa ttc tct ttg agt ggt gga aac tgg gac aat att tca gac gga    1970
Gly Lys Phe Ser Leu Ser Gly Gly Asn Trp Asp Asn Ile Ser Asp Gly
640                 645                 650                 655 gca aag gga gca atg gtt gca aca tac tct gcc ctg act cac aag acc    2018
Ala Lys Gly Ala Met Val Ala Thr Tyr Ser Ala Leu Thr His Lys Thr
                660                 665                 670 ttt caa cca gtc cta gag cct gta gct gct tca agc tta gcc cag cga    2066
Phe Gln Pro Val Leu Glu Pro Val Ala Ala Ser Ser Leu Ala Gln Arg
            675                 680                 685 cgg agc atg aaa aag cga aca tca act ggc ctg taagatttgt ggtgttccta   2119
Arg Ser Met Lys Lys Arg Thr Ser Thr Gly Leu
        690                 695 ggccaaactg gatgaagatg aaattaaatg tgtggctttt ttcctattct tatcaaaggc   2179
atcgttgtct gctaaattac ttgaatatta agtaatatta atccccatt tttagggggaa   2239 gtgagattta aaaaccatt cacaggtcca caatattcat actatgtgtt tgcagtagtg    2299
ttcaagtgtt tatttaagca tataattggt gtccaccagg tcctcacaac ttctctgcac   2359
acaagcttct aaaattcctt tcaaataaag ttactttaat attt                   2403

<210> SEQ ID NO 2
<211> LENGTH: 698
<212> TYPE: PRT
<213> ORGANISM: Homo sapiens
```

```
<400> SEQUENCE: 2

Met Leu Pro Phe Ala Pro Gln Asp Glu Pro Trp Asp Arg Glu Met Glu
1               5                   10                  15

Val Phe Ser Gly Gly Ala Ser Gly Glu Val Asn Gly Leu Lys
            20                  25                  30

Met Val Asp Glu Pro Met Glu Glu Gly Glu Ala Asp Ser Cys His Asp
            35                  40                  45

Glu Gly Val Val Lys Glu Ile Pro Ile Thr His His Val Lys Glu Gly
50                  55                  60

Tyr Glu Lys Ala Asp Pro Ala Gln Phe Glu Leu Leu Lys Val Leu Gly
65                  70                  75                  80

Gln Gly Ser Phe Gly Lys Val Phe Leu Val Arg Lys Thr Gly Pro
                85                  90                  95

Asp Ala Gly Gln Leu Tyr Ala Met Lys Val Leu Lys Lys Ala Ser Leu
            100                 105                 110

Lys Val Arg Asp Arg Val Arg Thr Lys Met Glu Arg Asp Ile Leu Val
            115                 120                 125

Glu Val Asn His Pro Phe Ile Val Lys Leu His Tyr Ala Phe Gln Thr
130                 135                 140

Glu Gly Lys Leu Tyr Leu Ile Leu Asp Phe Leu Arg Gly Gly Asp Val
145                 150                 155                 160

Phe Thr Arg Leu Ser Lys Glu Val Leu Phe Thr Glu Glu Asp Val Lys
                165                 170                 175

Phe Tyr Leu Ala Glu Leu Ala Leu Ala Leu Asp His Leu His Gln Leu
            180                 185                 190

Gly Ile Val Tyr Arg Asp Leu Lys Pro Glu Asn Ile Leu Leu Asp Glu
            195                 200                 205

Ile Gly His Ile Lys Leu Thr Asp Phe Gly Leu Ser Lys Glu Ser Val
            210                 215                 220

Asp Gln Glu Lys Lys Ala Tyr Ser Phe Cys Gly Thr Val Glu Tyr Met
225                 230                 235                 240

Ala Pro Glu Val Val Asn Arg Arg Gly His Ser Gln Ser Ala Asp Trp
                245                 250                 255

Trp Ser Tyr Gly Val Leu Met Phe Glu Met Leu Thr Gly Thr Leu Pro
            260                 265                 270

Phe Gln Gly Lys Asp Arg Asn Glu Thr Met Asn Met Ile Leu Lys Ala
            275                 280                 285

Lys Leu Gly Met Pro Gln Phe Leu Ser Ala Glu Ala Gln Ser Leu Leu
            290                 295                 300

Arg Met Leu Phe Lys Arg Asn Pro Ala Asn Arg Leu Gly Ser Glu Gly
305                 310                 315                 320

Val Glu Glu Ile Lys Arg His Leu Phe Phe Ala Asn Ile Asp Trp Asp
                325                 330                 335

Lys Leu Tyr Lys Arg Glu Val Gln Pro Pro Phe Lys Pro Ala Ser Gly
            340                 345                 350

Lys Pro Asp Asp Thr Phe Cys Phe Asp Pro Glu Phe Thr Ala Lys Thr
            355                 360                 365

Pro Lys Asp Ser Pro Gly Leu Pro Ala Ser Ala Asn Ala His Gln Leu
370                 375                 380

Phe Lys Gly Phe Ser Phe Val Ala Thr Ser Ile Ala Glu Glu Tyr Lys
385                 390                 395                 400

Ile Thr Pro Ile Thr Ser Ala Asn Val Leu Pro Ile Val Gln Ile Asn
            405                 410                 415
```

```
Gly Asn Ala Ala Gln Phe Gly Glu Val Tyr Glu Leu Lys Glu Asp Ile
            420                 425                 430

Gly Val Gly Ser Tyr Ser Val Cys Lys Arg Cys Ile His Ala Thr Thr
        435                 440                 445

Asn Met Glu Phe Ala Val Lys Ile Ile Asp Lys Ser Lys Arg Asp Pro
    450                 455                 460

Ser Glu Glu Ile Glu Ile Leu Met Arg Tyr Gly Gln His Pro Asn Ile
465                 470                 475                 480

Ile Thr Leu Lys Asp Val Phe Asp Asp Gly Arg Tyr Val Tyr Leu Val
                485                 490                 495

Thr Asp Leu Met Lys Gly Gly Glu Leu Leu Asp Arg Ile Leu Lys Gln
            500                 505                 510

Lys Cys Phe Ser Glu Arg Glu Ala Ser Asp Ile Leu Tyr Val Ile Ser
        515                 520                 525

Lys Thr Val Asp Tyr Leu His Cys Gln Gly Val Val His Arg Asp Leu
    530                 535                 540

Lys Pro Ser Asn Ile Leu Tyr Met Asp Glu Ser Ala Ser Ala Asp Ser
545                 550                 555                 560

Ile Arg Ile Cys Asp Phe Gly Phe Ala Lys Gln Leu Arg Gly Glu Asn
                565                 570                 575

Gly Leu Leu Leu Thr Pro Cys Tyr Thr Ala Asn Phe Val Ala Pro Glu
            580                 585                 590

Val Leu Met Gln Gln Gly Tyr Asp Ala Ala Cys Asp Ile Trp Ser Leu
        595                 600                 605

Gly Val Leu Phe Tyr Thr Met Leu Ala Gly Tyr Thr Pro Phe Ala Asn
    610                 615                 620

Gly Pro Asn Asp Thr Pro Glu Glu Ile Leu Leu Arg Ile Gly Asn Gly
625                 630                 635                 640

Lys Phe Ser Leu Ser Gly Gly Asn Trp Asp Asn Ile Ser Asp Gly Ala
                645                 650                 655

Lys Gly Ala Met Val Ala Thr Tyr Ser Ala Leu Thr His Lys Thr Phe
            660                 665                 670

Gln Pro Val Leu Glu Pro Val Ala Ala Ser Ser Leu Ala Gln Arg Arg
        675                 680                 685

Ser Met Lys Lys Arg Thr Ser Thr Gly Leu
    690                 695

<210> SEQ ID NO 3
<211> LENGTH: 2235
<212> TYPE: DNA
<213> ORGANISM: Homo sapiens
<220> FEATURE:
<221> NAME/KEY: CDS
<222> LOCATION: (1)..(2235)
<223> OTHER INFORMATION:

<400> SEQUENCE: 3 atg cta cca ttc gct cct cag gac gag ccc tgg gac cga gaa atg gaa      48
Met Leu Pro Phe Ala Pro Gln Asp Glu Pro Trp Asp Arg Glu Met Glu
1               5                   10                  15 gtg ttc agc ggc ggc ggc gcg agc agc ggc gag gta aat ggt ctt aaa      96
Val Phe Ser Gly Gly Gly Ala Ser Ser Gly Glu Val Asn Gly Leu Lys
            20                  25                  30 atg gtt gat gag cca atg gaa gag gga gaa gca gat tct tgt cat gat     144
Met Val Asp Glu Pro Met Glu Glu Gly Glu Ala Asp Ser Cys His Asp
        35                  40                  45
```

-continued

| | |
|---|---|
| gaa gga gtt gtt aaa gaa atc cct att act cat cat gtt aag gaa ggc<br>Glu Gly Val Val Lys Glu Ile Pro Ile Thr His His Val Lys Glu Gly<br>      50                            55                    60 | 192 |
| tat gag aaa gca gat cct gca cag ttt gag ttg ctc aag gtt ctt ggt<br>Tyr Glu Lys Ala Asp Pro Ala Gln Phe Glu Leu Leu Lys Val Leu Gly<br>65                   70                        75                 80 | 240 |
| cag ggg tca ttt gga aag gtt ttt ctt gtt aga aag aag acc ggt cct<br>Gln Gly Ser Phe Gly Lys Val Phe Leu Val Arg Lys Lys Thr Gly Pro<br>                      85                        90                       95 | 288 |
| gat gct ggg cag ctc tat gca atg aag gtg tta aaa aaa gcc tct tta<br>Asp Ala Gly Gln Leu Tyr Ala Met Lys Val Leu Lys Lys Ala Ser Leu<br>               100                      105                     110 | 336 |
| aaa gtt cga gac aga gtt cgg aca aag atg gag agg gat ata ctg gtg<br>Lys Val Arg Asp Arg Val Arg Thr Lys Met Glu Arg Asp Ile Leu Val<br>          115                      120                      125 | 384 |
| gaa gta aat cat cca ttt att gtc aaa ttg cac tat gcc ttt cag act<br>Glu Val Asn His Pro Phe Ile Val Lys Leu His Tyr Ala Phe Gln Thr<br>130                      135                      140 | 432 |
| gaa ggg aaa ctg tac tta ata ctg gat ttt ctc agg gga gga gat gtt<br>Glu Gly Lys Leu Tyr Leu Ile Leu Asp Phe Leu Arg Gly Gly Asp Val<br>145                      150                      155                      160 | 480 |
| ttc aca aga tta tcc aaa gag gtt ctg ttt aca gag gaa gat gtg aaa<br>Phe Thr Arg Leu Ser Lys Glu Val Leu Phe Thr Glu Glu Asp Val Lys<br>               165                      170                     175 | 528 |
| ttc tac ctc gca gaa ctg gcc ctt gct ttg gat cat ctg cac caa tta<br>Phe Tyr Leu Ala Glu Leu Ala Leu Ala Leu Asp His Leu His Gln Leu<br>          180                      185                     190 | 576 |
| gga att gtt tat aga gac ctg aag cca gaa aac att ttg ctt gat gaa<br>Gly Ile Val Tyr Arg Asp Leu Lys Pro Glu Asn Ile Leu Leu Asp Glu<br>               195                      200                     205 | 624 |
| ata gga cat atc aaa tta aca gat ttt gga ctc agc aag gag tca gta<br>Ile Gly His Ile Lys Leu Thr Asp Phe Gly Leu Ser Lys Glu Ser Val<br>          210                      215                     220 | 672 |
| gat caa gaa aag aag gct tac tca ttt tgt ggt aca gta gag tat atg<br>Asp Gln Glu Lys Lys Ala Tyr Ser Phe Cys Gly Thr Val Glu Tyr Met<br>225                      230                      235                      240 | 720 |
| gct cct gaa gta gta aat agg aga ggc cat tcc cag agt gct gat tgg<br>Ala Pro Glu Val Val Asn Arg Arg Gly His Ser Gln Ser Ala Asp Trp<br>               245                      250                     255 | 768 |
| tgg tca tat ggt gtt ctt atg ttt gaa atg ctt act ggt act ctg cca<br>Trp Ser Tyr Gly Val Leu Met Phe Glu Met Leu Thr Gly Thr Leu Pro<br>          260                      265                     270 | 816 |
| ttt caa ggt aaa gac aga aat gag acc atg aat atg ata tta aaa gca<br>Phe Gln Gly Lys Asp Arg Asn Glu Thr Met Asn Met Ile Leu Lys Ala<br>          275                      280                     285 | 864 |
| aaa ctt gga atg cct caa ttt ctt agt gct gaa gca caa agt ctt cta<br>Lys Leu Gly Met Pro Gln Phe Leu Ser Ala Glu Ala Gln Ser Leu Leu<br>290                      295                      300 | 912 |
| agg atg tta ttc aaa agg aat cca gca aat aga ttg gga tca gaa gga<br>Arg Met Leu Phe Lys Arg Asn Pro Ala Asn Arg Leu Gly Ser Glu Gly<br>305                      310                      315                      320 | 960 |
| gtt gaa gaa atc aaa aga cat ctg ttt ttt gca aat att gac tgg gat<br>Val Glu Glu Ile Lys Arg His Leu Phe Phe Ala Asn Ile Asp Trp Asp<br>               325                      330                     335 | 1008 |
| aaa tta tat aaa aga gaa gtt caa cct cct ttc aaa cct gct tct gga<br>Lys Leu Tyr Lys Arg Glu Val Gln Pro Pro Phe Lys Pro Ala Ser Gly<br>          340                      345                     350 | 1056 |
| aaa cca gat gat act ttt tgt ttt gat cct gaa ttt act gca aaa aca<br>Lys Pro Asp Asp Thr Phe Cys Phe Asp Pro Glu Phe Thr Ala Lys Thr<br>355                      360                      365 | 1104 |

```
cct aaa gat tct ccc ggt ttg cca gcc agt gca aat gct cat cag ctc       1152
Pro Lys Asp Ser Pro Gly Leu Pro Ala Ser Ala Asn Ala His Gln Leu
370                 375                 380 ttc aaa gga ttc agc ttt gtt gca act tct att gca gaa gaa tat aaa       1200
Phe Lys Gly Phe Ser Phe Val Ala Thr Ser Ile Ala Glu Glu Tyr Lys
385                 390                 395                 400 atc act cct atc aca agt gca aat gta tta cca att gtt cag ata aat       1248
Ile Thr Pro Ile Thr Ser Ala Asn Val Leu Pro Ile Val Gln Ile Asn
            405                 410                 415 gga aat gct gca caa ttt ggt gaa gta tat gaa ttg aag gag gat att       1296
Gly Asn Ala Ala Gln Phe Gly Glu Val Tyr Glu Leu Lys Glu Asp Ile
        420                 425                 430 ggt gtt ggc tcc tac tct gtt tgc aag cga tgc ata cat gca act acc       1344
Gly Val Gly Ser Tyr Ser Val Cys Lys Arg Cys Ile His Ala Thr Thr
    435                 440                 445 aac atg gaa ttt gca gtg aag atc att gac aaa agt aag cga gac cct       1392
Asn Met Glu Phe Ala Val Lys Ile Ile Asp Lys Ser Lys Arg Asp Pro
450                 455                 460 tca gaa gag att gaa ata ttg atg cgc tat gga caa cat ccc aac att       1440
Ser Glu Glu Ile Glu Ile Leu Met Arg Tyr Gly Gln His Pro Asn Ile
465                 470                 475                 480 att act ttg aag gat gtc ttt gat gat ggt aga tat gtt tac ctt gtt       1488
Ile Thr Leu Lys Asp Val Phe Asp Asp Gly Arg Tyr Val Tyr Leu Val
            485                 490                 495 acg gat tta atg aaa gga gga gag tta ctt gac cgt att ctc aaa caa       1536
Thr Asp Leu Met Lys Gly Gly Glu Leu Leu Asp Arg Ile Leu Lys Gln
        500                 505                 510 aaa tgt ttc tcg gaa cgg gag gct agt gat ata cta tat gta ata agt       1584
Lys Cys Phe Ser Glu Arg Glu Ala Ser Asp Ile Leu Tyr Val Ile Ser
    515                 520                 525 aag aca gtt gac tat ctt cat tgt caa gga gtt gtt cat cgt gat ctt       1632
Lys Thr Val Asp Tyr Leu His Cys Gln Gly Val Val His Arg Asp Leu
530                 535                 540 aaa cct agt aat att tta tac atg gat gaa tca gcc agt gca gat tca       1680
Lys Pro Ser Asn Ile Leu Tyr Met Asp Glu Ser Ala Ser Ala Asp Ser
545                 550                 555                 560 atc agg ata tgt gat ttt ggg ttt gca aaa caa ctt cga gga gaa aat       1728
Ile Arg Ile Cys Asp Phe Gly Phe Ala Lys Gln Leu Arg Gly Glu Asn
            565                 570                 575 gga ctt ctc tta act cca tgc tac act gca aac ttt gtt gca cct gag       1776
Gly Leu Leu Leu Thr Pro Cys Tyr Thr Ala Asn Phe Val Ala Pro Glu
        580                 585                 590 gtt ctt atg caa cag gga tat gat gct gct tgt gat atc tgg agt tta       1824
Val Leu Met Gln Gln Gly Tyr Asp Ala Ala Cys Asp Ile Trp Ser Leu
    595                 600                 605 gga gtc ctt ttt tac aca atg ttg gct ggc tac act cca ttt gct aat       1872
Gly Val Leu Phe Tyr Thr Met Leu Ala Gly Tyr Thr Pro Phe Ala Asn
610                 615                 620 ggc ccc aat gat act cct gaa gag ata ctg ctg cgt ata ggc aat gga       1920
Gly Pro Asn Asp Thr Pro Glu Glu Ile Leu Leu Arg Ile Gly Asn Gly
625                 630                 635                 640 aaa ttc tct ttg agt ggt gga aac tgg gac aat att tca gac gga gca       1968
Lys Phe Ser Leu Ser Gly Gly Asn Trp Asp Asn Ile Ser Asp Gly Ala
            645                 650                 655 aag gat ttg ctt tcc cat atg ctt cat atg gac cca cat cag cgg tat       2016
Lys Asp Leu Leu Ser His Met Leu His Met Asp Pro His Gln Arg Tyr
        660                 665                 670 act gct gaa caa ata tta aag cac tca tgg ata act cac aga gac cag       2064
Thr Ala Glu Gln Ile Leu Lys His Ser Trp Ile Thr His Arg Asp Gln
    675                 680                 685
```

```
ttg cca aat gat cag cca aag aga aat gat gtg tca cat gtt gtt aag    2112
Leu Pro Asn Asp Gln Pro Lys Arg Asn Asp Val Ser His Val Val Lys
    690                 695                 700 gga gca atg gtt gca aca tac tct gcc ctg act cac aag acc ttt caa    2160
Gly Ala Met Val Ala Thr Tyr Ser Ala Leu Thr His Lys Thr Phe Gln
705                 710                 715                 720 cca gtc cta gag cct gta gct gct tca agc tta gcc cag cga cgg agc    2208
Pro Val Leu Glu Pro Val Ala Ala Ser Ser Leu Ala Gln Arg Arg Ser
                725                 730                 735 atg aaa aag cga aca tca act ggc ctg                                2235
Met Lys Lys Arg Thr Ser Thr Gly Leu
            740                 745

<210> SEQ ID NO 4
<211> LENGTH: 745
<212> TYPE: PRT
<213> ORGANISM: Homo sapiens

<400> SEQUENCE: 4

Met Leu Pro Phe Ala Pro Gln Asp Glu Pro Trp Asp Arg Glu Met Glu
1               5                   10                  15

Val Phe Ser Gly Gly Ala Ser Ser Gly Glu Val Asn Gly Leu Lys
            20                  25                  30

Met Val Asp Glu Pro Met Glu Glu Gly Glu Ala Asp Ser Cys His Asp
            35                  40                  45

Glu Gly Val Val Lys Glu Ile Pro Ile Thr His His Val Lys Glu Gly
    50                  55                  60

Tyr Glu Lys Ala Asp Pro Ala Gln Phe Glu Leu Leu Lys Val Leu Gly
65                  70                  75                  80

Gln Gly Ser Phe Gly Lys Val Phe Leu Val Arg Lys Lys Thr Gly Pro
                85                  90                  95

Asp Ala Gly Gln Leu Tyr Ala Met Lys Val Leu Lys Lys Ala Ser Leu
            100                 105                 110

Lys Val Arg Asp Arg Val Arg Thr Lys Met Glu Arg Asp Ile Leu Val
        115                 120                 125

Glu Val Asn His Pro Phe Ile Val Lys Leu His Tyr Ala Phe Gln Thr
    130                 135                 140

Glu Gly Lys Leu Tyr Leu Ile Leu Asp Phe Leu Arg Gly Gly Asp Val
145                 150                 155                 160

Phe Thr Arg Leu Ser Lys Glu Val Leu Phe Thr Glu Glu Asp Val Lys
                165                 170                 175

Phe Tyr Leu Ala Glu Leu Ala Leu Ala Leu Asp His Leu His Gln Leu
            180                 185                 190

Gly Ile Val Tyr Arg Asp Leu Lys Pro Glu Asn Ile Leu Leu Asp Glu
        195                 200                 205

Ile Gly His Ile Lys Leu Thr Asp Phe Gly Leu Ser Lys Glu Ser Val
    210                 215                 220

Asp Gln Glu Lys Lys Ala Tyr Ser Phe Cys Gly Thr Val Glu Tyr Met
225                 230                 235                 240

Ala Pro Glu Val Val Asn Arg Arg Gly His Ser Gln Ser Ala Asp Trp
                245                 250                 255

Trp Ser Tyr Gly Val Leu Met Phe Glu Met Leu Thr Gly Thr Leu Pro
            260                 265                 270

Phe Gln Gly Lys Asp Arg Asn Glu Thr Met Asn Met Ile Leu Lys Ala
        275                 280                 285
```

```
Lys Leu Gly Met Pro Gln Phe Leu Ser Ala Glu Ala Gln Ser Leu Leu
290                 295                 300

Arg Met Leu Phe Lys Arg Asn Pro Ala Asn Arg Leu Gly Ser Glu Gly
305                 310                 315                 320

Val Glu Glu Ile Lys Arg His Leu Phe Phe Ala Asn Ile Asp Trp Asp
                325                 330                 335

Lys Leu Tyr Lys Arg Glu Val Gln Pro Pro Phe Lys Pro Ala Ser Gly
            340                 345                 350

Lys Pro Asp Asp Thr Phe Cys Phe Asp Pro Glu Phe Thr Ala Lys Thr
        355                 360                 365

Pro Lys Asp Ser Pro Gly Leu Pro Ala Ser Ala Asn Ala His Gln Leu
    370                 375                 380

Phe Lys Gly Phe Ser Phe Val Ala Thr Ser Ile Ala Glu Glu Tyr Lys
385                 390                 395                 400

Ile Thr Pro Ile Thr Ser Ala Asn Val Leu Pro Ile Val Gln Ile Asn
                405                 410                 415

Gly Asn Ala Ala Gln Phe Gly Glu Val Tyr Glu Leu Lys Glu Asp Ile
            420                 425                 430

Gly Val Gly Ser Tyr Ser Val Cys Lys Arg Cys Ile His Ala Thr Thr
        435                 440                 445

Asn Met Glu Phe Ala Val Lys Ile Ile Asp Lys Ser Lys Arg Asp Pro
450                 455                 460

Ser Glu Glu Ile Glu Ile Leu Met Arg Tyr Gly Gln His Pro Asn Ile
465                 470                 475                 480

Ile Thr Leu Lys Asp Val Phe Asp Asp Gly Arg Tyr Val Tyr Leu Val
                485                 490                 495

Thr Asp Leu Met Lys Gly Gly Glu Leu Leu Asp Arg Ile Leu Lys Gln
            500                 505                 510

Lys Cys Phe Ser Glu Arg Glu Ala Ser Asp Ile Leu Tyr Val Ile Ser
        515                 520                 525

Lys Thr Val Asp Tyr Leu His Cys Gln Gly Val Val His Arg Asp Leu
    530                 535                 540

Lys Pro Ser Asn Ile Leu Tyr Met Asp Glu Ser Ala Ser Ala Asp Ser
545                 550                 555                 560

Ile Arg Ile Cys Asp Phe Gly Phe Ala Lys Gln Leu Arg Gly Glu Asn
                565                 570                 575

Gly Leu Leu Leu Thr Pro Cys Tyr Thr Ala Asn Phe Val Ala Pro Glu
            580                 585                 590

Val Leu Met Gln Gln Gly Tyr Asp Ala Ala Cys Asp Ile Trp Ser Leu
        595                 600                 605

Gly Val Leu Phe Tyr Thr Met Leu Ala Gly Tyr Thr Pro Phe Ala Asn
    610                 615                 620

Gly Pro Asn Asp Thr Pro Glu Glu Ile Leu Leu Arg Ile Gly Asn Gly
625                 630                 635                 640

Lys Phe Ser Leu Ser Gly Gly Asn Trp Asp Asn Ile Ser Asp Gly Ala
                645                 650                 655

Lys Asp Leu Leu Ser His Met Leu His Met Asp Pro His Gln Arg Tyr
            660                 665                 670

Thr Ala Glu Gln Ile Leu Lys His Ser Trp Ile Thr His Arg Asp Gln
        675                 680                 685

Leu Pro Asn Asp Gln Pro Lys Arg Asn Asp Val Ser His Val Val Lys
    690                 695                 700
```

-continued

```
Gly Ala Met Val Ala Thr Tyr Ser Ala Leu Thr His Lys Thr Phe Gln
705                 710                 715                 720

Pro Val Leu Glu Pro Val Ala Ala Ser Ser Leu Ala Gln Arg Arg Ser
            725                 730                 735

Met Lys Lys Arg Thr Ser Thr Gly Leu
            740                 745

<210> SEQ ID NO 5
<211> LENGTH: 22
<212> TYPE: DNA
<213> ORGANISM: Homo sapiens

<400> SEQUENCE: 5
ggagcaaagg gagcaatggt tg                                          22

<210> SEQ ID NO 6
<211> LENGTH: 22
<212> TYPE: DNA
<213> ORGANISM: Homo sapiens

<400> SEQUENCE: 6
tcttcatcca gtttggccta gg                                          22

<210> SEQ ID NO 7
<211> LENGTH: 20
<212> TYPE: DNA
<213> ORGANISM: Homo sapiens

<400> SEQUENCE: 7
tgggtgtgaa ccatgagaag                                             20

<210> SEQ ID NO 8
<211> LENGTH: 20
<212> TYPE: DNA
<213> ORGANISM: Homo sapiens

<400> SEQUENCE: 8
gtgtcgctgt tgaagtcaga                                             20
```

What is claimed is:

1. An isolated nucleic acid comprising the nucleotide sequence of SEQ ID NO: 1.

2. An expression vector comprising the nucleic acid of claim 1.

3. A host cell comprising the expression vector of claim 2.

4. A method for producing an isolated polypeptide comprising the amino acid sequence of SEQ ID NO: 2, which comprises the steps of:
   (1) culturing the host cell of claim 3 under a condition suitable for the expression of the polypeptide; and
   (2) recovering the polypeptide from the host cell culture.

5. A method for detecting the presence of an isolated nucleic acid of claim 1 for diagnosing T-cell lymphoblastic lymphoma in a mammal, which comprises the steps of:
   (1) extracting total RNA from a sample obtained from the mammal;
   (2) amplifying the RNA by reverse transcriptase-polymerase chain reaction (RT-PCR) to obtain a cDNA sample; and
   (3) detecting whether the nucleic acid of claim 1 is obtained.

* * * * *